US009556248B2

(12) United States Patent
Cochran et al.

(10) Patent No.: US 9,556,248 B2
(45) Date of Patent: Jan. 31, 2017

(54) HEPATOCYTE GROWTH FACTOR FRAGMENTS THAT FUNCTION AS POTENT MET RECEPTOR AGONISTS AND ANTAGONISTS

(75) Inventors: Jennifer R. Cochran, Stanford, CA (US); Douglas S. Jones, II, Stanford, CA (US); Ping-Chuan Tsai, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/636,053

(22) PCT Filed: Mar. 21, 2011

(86) PCT No.: PCT/US2011/029271
§ 371 (c)(1),
(2), (4) Date: Dec. 28, 2012

(87) PCT Pub. No.: WO2011/116396
PCT Pub. Date: Sep. 22, 2011

(65) Prior Publication Data
US 2013/0171068 A1  Jul. 4, 2013

Related U.S. Application Data

(60) Provisional application No. 61/315,794, filed on Mar. 19, 2010, provisional application No. 61/411,080, filed on Nov. 8, 2010.

(51) Int. Cl.
| | | |
|---|---|---|
| *A61K 38/18* | (2006.01) | |
| *C07K 14/475* | (2006.01) | |
| *A61K 38/00* | (2006.01) | |

(52) U.S. Cl.
CPC ........... *C07K 14/4753* (2013.01); *A61K 38/00* (2013.01)

(58) Field of Classification Search
CPC .................. C07K 14/4753; A61K 38/1833
See application file for complete search history.

(56) References Cited

U.S. PATENT DOCUMENTS

| 7,179,786 B2 * | 2/2007 | Gherardi et al. ............ 514/13.7 |
| 2009/0215686 A1 * | 8/2009 | Xu et al. ........................ 514/12 |

FOREIGN PATENT DOCUMENTS

WO  WO 02/088354 A1  11/2002

OTHER PUBLICATIONS

Gherardi et al., PNAS, 103(11):4046-4051, 2006.*
Gai, S. Annie and Wittrup, K. Dane, "Yeast surface display for protein engineering and characterization," *Current Opinion in Structural Biology*, 17:4 pp. 467-473 (2007).
Jones et al., "Developing therapeutic proteins by engineering ligand-receptor interactions," *Trends in Biotechnology*, 26:9, pp. 498-505 (2008).
Jones, Douglas S. and Cochran, Jennifer R., "Engineered Hepatocyte Growth Factor Fragments Function as Met Receptor Antagonists by Inhibiting Ligand-Induced Dimerization," *AIChE Annual Meeting*, (2010).
Jones et al., "Engineering hepatocyte growth factor fragments with high stability and activity as Met receptor agonists and antagonists," *PNAS*, 108:32, pp. 13035-13040 (2011).
Youles et al., "Engineering the NK1 Fragment of Hepatocyte Growth Factor/Scatter Factor as a Met Receptor Antagonist," *J. Mol. Biol.*, 377:3, pp. 616-622 (2008).

* cited by examiner

*Primary Examiner* — Marianne P Allen
(74) *Attorney, Agent, or Firm* — Morgan, Lewis & Bockius LLP

(57) ABSTRACT

The NK1 fragment of hepatocyte growth factor (HGF) binds to and activates the Met receptor, a transmembrane receptor tyrosine kinase that plays a critical role in embryonic development and organ formation. The instant application discloses NK1 variant polypeptides which act as agonists or antagonists of HGF. Further disclosed are covalently linked NK1 variant polypeptides. Many of the disclosed variant polypeptides possess improved stability characteristics.

20 Claims, 19 Drawing Sheets

HEPATOCYTE GROWTH FACTOR FRAGMENTS THAT FUNCTION AS POTENT MET RECEPTOR AGONISTS AND ANTAGONISTS

PRIORITY CLAIM

This application claims priority to U.S. provisional patent application, Ser. No. 61/315,794, filed Mar. 19, 2010, U.S. provisional patent application, Ser. No. 61/411,080, filed Nov. 8, 2010, and International Patent Application No. PCT/US2011/029271, filed Mar. 21, 2011, the contents of which are incorporated in their entirety.

STATEMENT OF GOVERNMENT RIGHTS

This invention was made with Government support under contracts CA131706 and CA151706 awarded by the National Institutes of Health. The Government has certain rights in this invention.

FIELD OF THE INVENTION

The invention pertains to the field of polypeptide variants, in particular variants of Hepatocyte Growth Factor.

BACKGROUND OF THE INVENTION

Hepatocyte Growth Factor (HGF), also known as Scatter Factor (SF), is a multi-functional heterodimeric protein produced predominantly by mesenchymal cells and is an effector of cells expressing the Met tyrosine kinase receptor ("c-Met")(Bottaro et al. (1991) SCIENCE 251: 802-804, Rubin et al. (1993) BIOCHIM. BIOPHYS. ACTA 1155: 357-371). Mature HGF contains two polypeptide chains, the α-chain and the β-chain. Published studies suggest it is the α-chain that contains HGF's c-Met receptor binding domain.

Mature HGF contains two polypeptide chains, the α-chain and the β-chain. Upon binding to its cognate receptor, HGF mediates a number of cellular activities. The HGF-Met signaling pathway plays a role in liver regeneration, wound healing, neural regeneration, angiogenesis and malignancies. See, e.g., Cao et al. (2001) PROC. NATL. ACAD. SCI. USA 98: 7443-7448, Burgess et al. (2006) CANCER RES. 66: 1721-1729, and U.S. Pat. Nos. 5,997,868 and 5,707,624.

Dysregulation of cell signaling pathways that mediate proliferation, survival, and migration are an underlying cause of many cancers. In particular, dysregulation and over-expression of the Met tyrosine kinase receptor correlates to poor prognosis in many human tumors, making it an attractive target for therapeutic intervention.

There are currently no FDA approved therapeutics targeting the Met receptor, however, a few candidate molecules are in various stages of clinical trials. As such, molecules that potently inhibit Met receptor activation may have a significant impact on cancer therapy. In addition, studies to develop Met-targeted molecular imaging agents for non-invasive visualization of Met expression in vivo have been extremely limited compared to other cancer targets. The availability of such imaging agents would aid in cancer diagnosis, staging, and disease management, as well as help identify patients who would be good candidates for Met-targeted therapies.

The present invention provides potent activators and inhibitors of the Met receptor, methods for their production and use.

SUMMARY OF THE INVENTION

Hepatocyte growth factor is active in numerous tissues throughout the body, participating in the regulation of angiogenesis, organogenesis, tissue repair and neural induction. HGF induces random movement ("scatter") when applied to epithelial cells as well as dissociation, migration, and invasion of cells through the extracellular matrix in vivo. HGF is mitogenic (induces proliferation) in many normal cell types, including epithelial cells, vascular endothelial cells, and melanocytes.

HGF is also a morphogen that induces transition of epithelial cells into a mesenchymal (connective tissue-type) morphology and formation of branched tube-like structures; these cellular responses reflect this cytokine's role in organogenesis and tissue repair.

HGF is cytoprotective by virtue of its anti-apoptotic activity and exerts anti-fibrotic effects by opposing TGFβ1-Smad signaling.

Each of these biological effects exerted by HGF is triggered by stimulating its cell surface receptor c-Met with concomitant activation of downstream effector pathways The Met receptor is the product of the protooncogene met. Met is the cognate receptor for HGF. Dysregulation of HGF-Met signaling results in a phenotype of invasion and metastasis in many human tumors. Cell lines engineered to express high levels of mutated Met or wild-type Met and HGF (autocrine signaling) become tumorigenic and metastatic. In addition, transgenic mouse models that express Met, HGF, or mutated Met, develop different types of tumors and metastatic lesions.

Met overexpression has been found in many human cancers, including colorectal cancer, oral squamous cell carcinoma, hepatocellular carcinoma, renal cell carcinoma, breast carcinoma and lung carcinoma. Since Met overexpression correlates to poor clinical prognosis, this receptor is an attractive target for cancer diagnosis and therapy.

The development of clinical agents that target Met has been difficult. Monoclonal antibodies cross-link the Met receptor, resulting in receptor signalling, while kinase domain inhibitors lack target specificity.

In previous approaches, novel strategies to create hepatocyte growth factor (HGF) or HGF fragment-based antagonists have been promising and have highlighted the potential to develop potent therapeutics by inhibiting HGF-mediated Met activation. While these molecules opened up new research directions for testing and generating new cancer biologics, they have not advanced to clinical trials due to limitations in Met receptor binding affinity, recombinant expression yield, and/or protein stability.

Alternatively, agonists of c-Met should promote tissue repair and organ regeneration in two ways: first, as a prophylactic, by protecting healthy cells from both necrotic and apoptotic death; and second, as a therapeutic, by promoting appropriate cell proliferation and migration needed for repair of pre-existing tissue injury. HGF agonists offer new therapeutic approaches to protecting major organs (including the liver, kidney, lung, heart, brain, and spinal cord) from injury, and reducing fibrosis in the liver, kidney, lung, and heart.

The present invention provides a solution to these problems in the provision of polypeptide variants of Hepatocyte Growth Factor. In various embodiments, variant HGF polypeptides are provided that form covalently linked dimers. These covalent dimers result from the introduction of novel sulfhydryl reactive groups.

In addition to the polypeptide variants, the invention provides methods of tissue regeneration using the variants. The method includes contacting cells with a therapeutically or prophylatically effective amount of a HGF variant of the invention.

There is also a need for therapeutic agents that modulate the activity of Met. Accordingly, the present invention also provides HGF variants in a pharmaceutical formulation.

Other advantages, aspects and objects of the invention are apparent from the detailed description which follows.

The dimer peak was collected and used for subsequent cellular activity assays. B) SDS-PAGE of purified cdD127N and cdD127K proteins. Non-reduced NK1 proteins (left two lanes) and reduced with β-mercaptoethanol right two lanes), supporting that the covalent dimers are the result of disulfide bonds. SDS-PAGE lane order: (L-R) Size marker, cdD127K (non-reduced), cdD127N (non-reduced), cdD127K (reduced), cdD127N (reduced). cdD127N: cystine dimer M2.2 D127N; cdD127K: cystine dimer M2.2 D127K.

Figure 17:
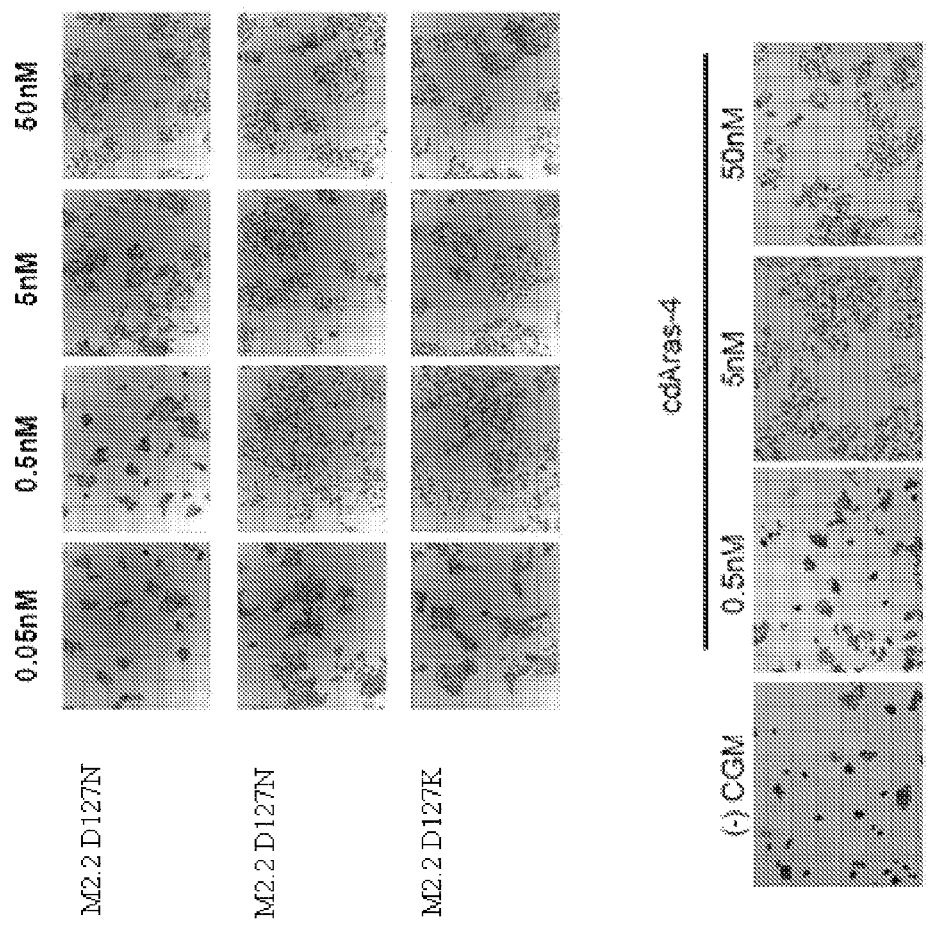

FIG. 17: Covalently coupled NK1 Homodimers Are Potent Agonists. (top) MDCK scatter activity of the M2.2 D127N monomer (without the free cysteine residue) or the cystine dimer proteins. cdD127N: cystine dimer M2.2 D127N; cdD127K: cystine dimer M2.2 D127K. (bottom) Cystine dimerization of Aras-4 (cdAras-4) as transforms Aras-4 from an antagonist to a potent agonist.

Figure 18A:
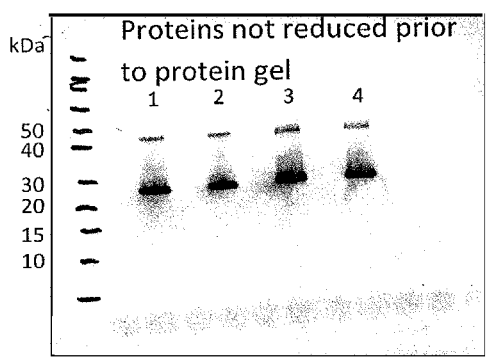
Figure 18B:
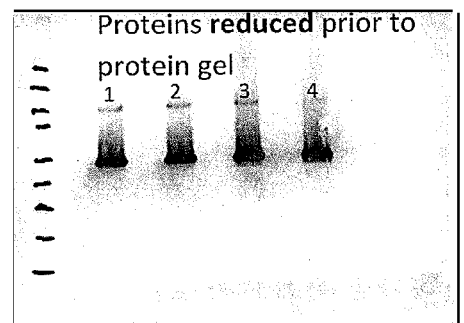

FIG. 18: Western Blots of Aras-4 D127C. (A) Proteins not reduced prior to addition to gel (B) Proteins reduced prior to addition to gel. Lane1 Aras-4 untreated; Lane 2 Aras-4 copper phenathroline treated; Aras-4 D127C untreated; Lane 4 Aras-4 D127C copper phenanthroline treated.

Figure 19:
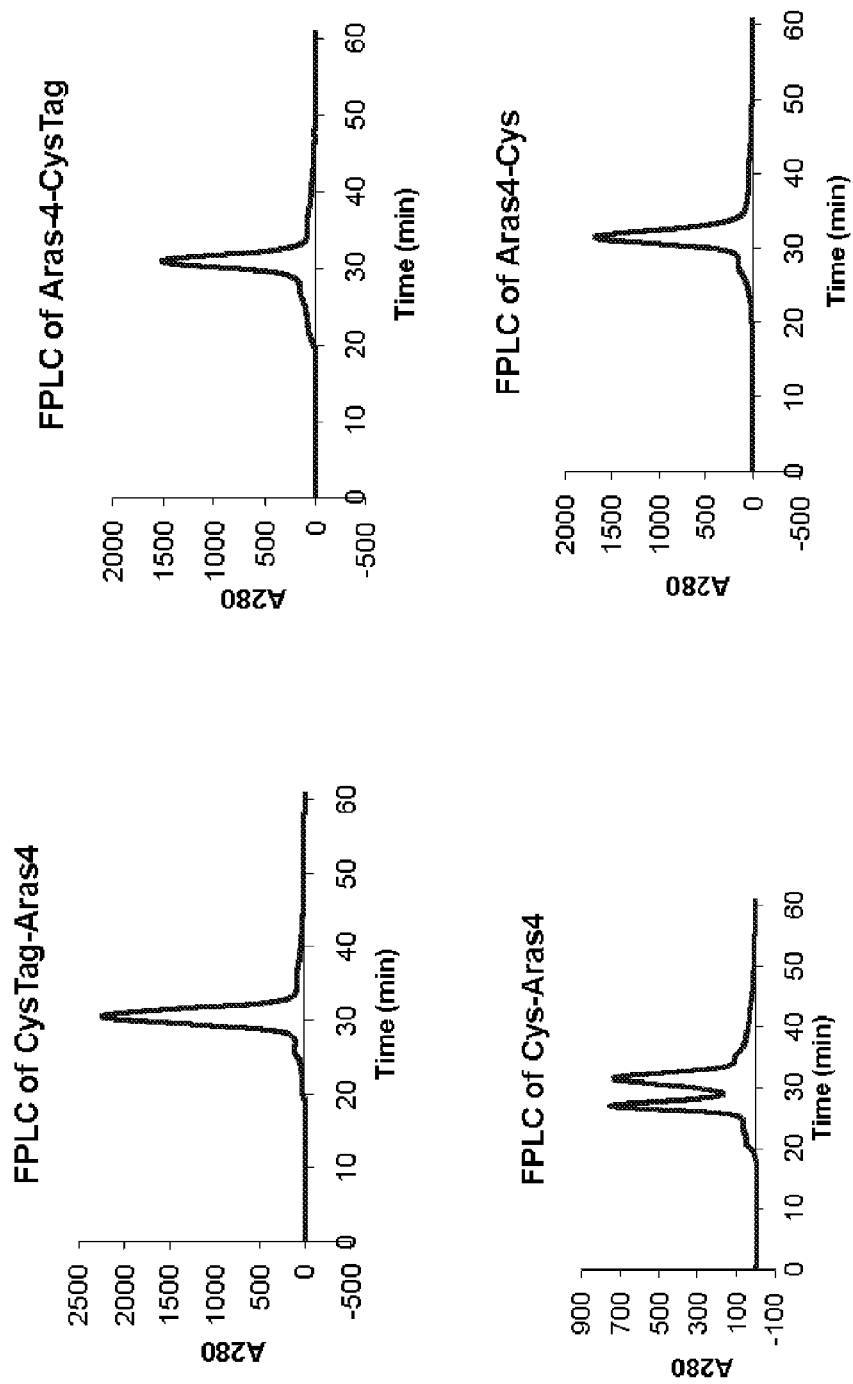

FIG. 19: Only an N-terminal Cysteine Mediates NK1 Homodimerization Directly from Yeast Cultures.

DETAILED DESCRIPTION OF THE INVENTION

I. Introduction

The Met receptor is expressed from a single gene product and is proteolytically processed into a 50 kD α-chain and a 140 kD β-chain. The α-chain and first 212 residues of the β-chain comprise the Sema domain, a complex 7-bladed β-propeller fold. The remainder of the Met β-chain comprises a cysteine-rich domain, four immunoglobulin domains, an intracellular kinase domain, and a C-terminal tail. Upon ligand binding and dimerization, Met is cross-phosphorylated on Tyr-1234 and Tyr-1235 of the intracellular kinase domain. This activity results in further phosphorylation of Tyr-1349 and Tyr-1356 at the C-terminus of Met, which is a multisubstrate docking site for adapter proteins and signal transducers Shc, Grb2, Gab1, PI-3 kinase and PLC-γ.

Figure 1:
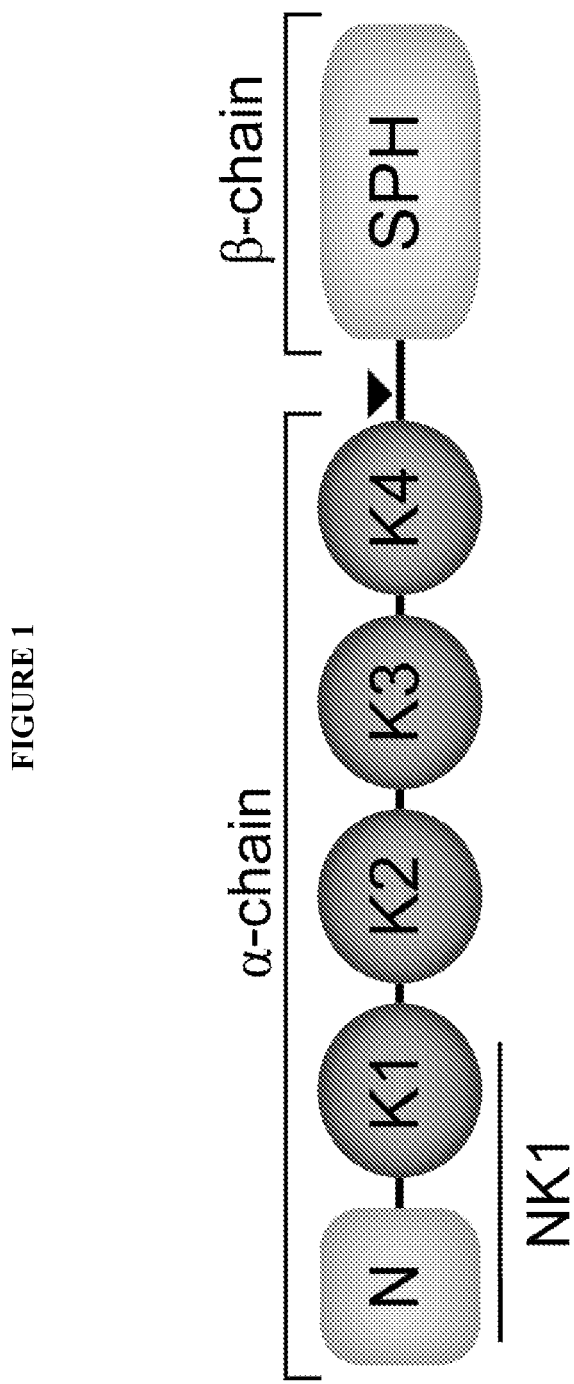
FIG. 1: HGF domain structure. N: N-terminal PAN module; K: Kringle domain; SPH: serine protease homology domain. Black arrow indicates cleavage site to cleave HGF into its two-chain active form. The α- and β-chains are connected through a disulfide bond. The N-terminal and first Kringle domain comprise the NK1 fragment of HGF.

HGF exhibits an overall domain structure similar to coagulation factors such as plasminogen; it is expressed as a single-chain inactive precursor, which must be cleaved into its functionally active form by enzymes such as HGF activator, matriptase, hepsin, Factor XIIa, and Factor Xia. Single-chain proHGF and the cleaved two-chain HGF both bind Met with high affinity, but only two-chain HGF is capable of inducing Met activation. The HGF α-chain is comprised of an N-terminal hairpin-containing domain (PAN module; apple domain), followed by four Kringle domains (FIG. 1). The HGF β-chain consists of a serine protease homology domain, but lacks catalytic activity due to absence of key residues in the catalytic triad.

Several HGF fragments have been reported; NK1 and NK2 are naturally occurring HGF splice-variants, and NK4 was initially discovered through digestion of HGF with pancreatic elastase. These fragments are comprised of the N-terminal and first Kringle (NK1), first and second Kringle (NK2), or first through fourth Kringle (NK4) domains. NK1 and NK2 were were first reported to be Met antagonists, but have since been determined to function as weak Met agonists. In contrast, NK4 maintains strong binding to Met (400-600 pM), but does not induce Met activation, and thereby functions as a competitive HGF antagonist. NK1 appears to comprise the minimal function unit of HGF, as it binds and activates Met, albeit much more weakly than full-length HGF.

The present invention provides numerous advantages not present in known Met binding agents. For example, in various embodiments, the engineered polypeptide variants of the invention bind to the Met receptor with high affinity, possess high stability, and can be produced from microbial cultures at yields >10 mg/L. Moreover, these engineered variants also potently inhibit HGF-induced Met activation. Because the variants target the receptor directly, they are also of use in vivo and in vitro molecular imaging agents for diagnostic applications.

In an exemplary embodiment, the variants are prepared by conducting rounds of directed evolution of HGF, or a portion thereof, comprising at least it's N-terminal and first Kringle domain (NK1), for improvements in Met binding affinity and thermal stability.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures of analytical and synthetic organic chemistry described below are those well known and commonly employed in the art. Standard techniques, or modifications thereof, are used for chemical syntheses and chemical analyses.

The terms "M2.1" and "M2.2" refer to variants of SEQ. ID. NO.: 1 having the following substitutions: (i) $K_{62}E$, N127D, K137R, K170E, N193D; and (ii) K62E, Q95R, N127D, K132N, K137R, K170E, Q173R, N193D, respectively.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term nucleic acid is used interchangeably with gene, cDNA, and mRNA encoded by a gene. Moreover, as used herein, a nucleic acid encoding a polypeptide variant of the invention is defined to include the nucleic acid sequence complementary to this nucleic acid sequence.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. An isolated nucleic acid can be a component of an expression vector.

Typically, isolated polypeptides of the invention have a level of purity preferably expressed as a range. The lower end of the range of purity for the polypeptide is about 60%, about 70% or about 80% and the upper end of the range of purity is about 70%, about 80%, about 90% or more than about 90%.

When the polypeptides are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, mass-spectroscopy, or a similar means).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), H is (H), Glu (E), Asn (N), Gln (O), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include H is (H), Arg (R) and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Tip (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C (O)R, —C(O)OH, —C(O)OR, —C(O)NH$_2$, —C(O)NHR, —C(O)NRR and the like where each R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_1$-$C_{21}$)) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Tip (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfonyl-containing amino acids. The ability of Cys (C) residues (and other amino acids with —SH containing side chains) to exist in a peptide in either the reduced free-SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the present invention Cys (C) is categorized as a polar hydrophilic amino acid, notwithstanding the general classifications defined above.

The term "linker" refers to an amino-acid polypeptide spacer that covalently links two or more polypeptides. The linker can be 1-15 amino acid residues. Preferably the linker is a single cysteine residue. The linker can also have the amino acid sequence SEQ ID NO:24 KESCAKKQRQHMDS.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

Certain amino acid residues, called "helix breaking" amino acids, have a propensity to disrupt the structure of a-helices when contained at internal positions within the helix. Amino acid residues exhibiting such helix-breaking properties are well-known in the art (see, e.g., Chou and Fasman, Ann. Rev. Biochem. 47:251-276) and include Pro (P), Gly (G) and potentially all D-amino acids (when contained in an L-peptide; conversely, L-amino acids disrupt helical structure when contained in a D-peptide) as well as a proline analogue. While these helix-breaking amino acid residues fall into the categories defined above, with the exception of Gly (G) (discussed infra), these residues should not be used to substitute amino acid residues at internal positions within the helix—they should only be used to substitute 1-3 amino acid residues at the N-terminus and/or C-terminus of the peptide.

While the above-defined categories have been exemplified in terms of the genetically encoded amino acids, the amino acid substitutions need not be, and in certain embodiments preferably are not, restricted to the genetically encoded amino acids. Indeed, many of the preferred peptides of formula (I) contain genetically non-encoded amino acids. Thus, in addition to the naturally occurring genetically encoded amino acids, amino acid residues in the core peptides of formula (I) may be substituted with naturally occurring non-encoded amino acids and synthetic amino acids.

Certain commonly encountered amino acids which provide useful substitutions for the core peptides of formula (I) include, but are not limited to, β-alanine(β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe (4-Cl)); 2-fluorophenylalanine (Phe (2-F)); 3-fluorophenylalanine (Phe (3-F)); 4-fluorophenylalanine (Phe (4-F)); penicillamine (Pen); 1/2/3/4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH$_2$)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines). In addition, in some embodiments the amino acid proline in the core peptides of formula (I) is substantiated with a proline analogue, including, but not limited to, azetidine-2-carboxylate (A2C), L-Thiazolidine-4-carboxylic Acid, cis-4-hydroxy-L-proline (CHP), 3,4-dehydroproline, thioproline, and isonipecotic acid (Inp).

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, H is), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure, therefore, consider functional or biological equivalents of a polypeptide or protein as set forth above. In particular, embodiments of the invention provides variants having about 50%, 60%, 70%, 80%, 90%, and 95% sequence identity to the parent polypeptide. In various embodiments, the invention provides variants having this level of identity to a portion of the parent polypeptide sequence, e.g., NK1, as defined herein. In various embodiments, the variant has at least about 95%, 96%, 97%, 98% or 99% sequence identity to the parent polypeptide or to a portion of the parent polypeptide sequence, e.g., NK1, as defined herein.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

"Identity," as known in the art, is a relationship between two or more polypeptide or protein sequences, as determined by comparing the sequences. In the art, "identity" also refers to the degree of sequence relatedness between polypeptides or proteins, as determined by the match between strings of such sequences. "Identity" can be readily calculated by known bioinformational methods.

"Peptide" refers to a polymer in which the monomers are amino acids and are joined together through amide bonds. Peptides of the present invention can vary in size, e.g., from two amino acids to hundreds or thousands of amino acids. A larger peptide (e.g., at least 10, at least 20, at least 30 or at least 50 amino acid residues) is alternatively referred to as a "polypeptide" or "protein". Additionally, unnatural amino acids, for example, β-alanine, phenylglycine, homoarginine and homophenylalanine are also included. Amino acids that are not gene-encoded may also be used in the present invention. Furthermore, amino acids that have been modified to include reactive groups, glycosylation sequences, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" or "polypeptide" refers to both glycosylated and non-glycosylated peptides or "polypeptides". Also included are polypetides that are incompletely glycosylated by a system that expresses the polypeptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

In the present application, amino acid residues are numbered (typically in the superscript) according to their relative positions from the N-terminal amino acid (e.g., N-terminal methionine) of the polypeptide, which is numbered "1". The N-terminal amino acid may be a methionine (M), numbered "1". The numbers associated with each amino acid residue can be readily adjusted to reflect the absence of N-terminal methionine if the N-terminus of the polypeptide starts without a methionine. It is understood that the N-terminus of an exemplary polypeptide can start with or without a methionine. Accordingly, in instances in which an amino acid linker is added to the N-terminus of a wild-type polypeptide, the first linker amino acid adjoined to the N-terminal amino acid is number −1 and so forth. For example, if the linker has the amino acid sequence SEQ ID NO:24 KESCAKKQRQH-MDS, with the S residue adjoined to the N-terminal amino acid of the wild-type polypeptide, then the most N-terminal linker amino acid K would be −14, while the most C-terminal linker amino acid S would be −1. In this way, the numbering of amino acids in the wild type polypeptide and linker bound wild type polypeptide is preserved.

The term "parent polypeptide" refers to a wild-type polypeptide and the amino acid sequence or nucleotide sequence of the wild-type polypeptide is part of a publicly accessible protein database (e.g., EMBL Nucleotide Sequence Database, NCBI Entrez, ExPasy, Protein Data Bank and the like).

The term "mutant polypeptide" or "polypeptide variant" or "mutein" refers to a form of a polypeptide, wherein its amino acid sequence differs from the amino acid sequence of its corresponding wild-type (parent) form, naturally existing form or any other parent form. A mutant polypeptide can contain one or more mutations, e.g., replacement, insertion, deletion, etc. which result in the mutant polypeptide.

The term "corresponding to a parent polypeptide" (or grammatical variations of this term) is used to describe a polypeptide of the invention, wherein the amino acid sequence of the polypeptide differs from the amino acid sequence of the corresponding parent polypeptide only by the presence of at least amino acid variation. Typically, the amino acid sequences of the variant polypeptide and the parent polypeptide exhibit a high percentage of identity. In one example, "corresponding to a parent polypetide" means that the amino acid sequence of the variant polypeptide has at least about 50% identity, at least about 60%, at least about 70%, at least about 80%, at least about 90%, at least about 95% or at least about 98% identity to the amino acid sequence of the parent polypeptide. In another example, the nucleic acid sequence that encodes the variant polypeptide has at least about 50% identity, at least about 60%, at least about 70%, at least about 80%, at least about 90%, at least about 95% or at least about 98% identity to the nucleic acid sequence encoding the parent polypeptide.

The term "introducing (or adding etc.) a variation into a parent polypeptide" (or grammatical variations thereof), or "modifying a parent polypeptide" to include a variation (or grammatical variations thereof) do not necessarily mean that the parent polypeptide is a physical starting material for such conversion, but rather that the parent polypeptide provides the guiding amino acid sequence for the making of a variant polypeptide. In one example, "introducing a variant into a parent polypeptide" means that the gene for the parent polypeptide is modified through appropriate mutations to create a nucleotide sequence that encodes a variant polypeptide. In another example, "introducing a variant into a parent polypeptide" means that the resulting polypeptide is theoretically designed using the parent polypeptide sequence as a guide. The designed polypeptide may then be generated by chemical or other means.

As used herein "NK1" consists of the N-terminal and first Kringle domains of hepatocyte growth factor. Break points in the polypeptides of the present invention include amino acids 28-210 of human hepatocyte growth factor Isoform 1 (Genbank Acession ID NP_000592). Others have used break points of 31-210 and 32-210. An alternative human hepatocyte growth factor isoform, Isoform 3 (Genbank Accession ID NP_00101932.1) is identical to human HGF (hHGF) Isoform 1, except for a 5 amino acid deletion in the first Kringle domain. hHGF Isoform 1 and Isoform 3 both potently activate the Met receptor and NK1 proteins derived from hHGF Isoform 1 or Isoform 3 also both bind and activate the Met receptor. Break points of 28-205, 31-205, and 32-205 for NK1 based on Isoform 3 variant would be identical to break points of 28-210, 31-210, and 32-210 for NK1 based on the Isoform 1 variant, with the only difference being the deletion of 5 amino acids from the first kringle domain (K1).

The term "library" refers to a collection of different polypeptides each corresponding to a common parent polypeptide. Each polypeptide species in the library is referred to as a member of the library. Preferably, the library of the present invention represents a collection of polypeptides of sufficient number and diversity to afford a population from which to identify a lead polypeptide. A library includes at least two different polypeptides. In one embodiment, the library includes from about 2 to about 100,000,000 members. In another embodiment, the library includes from about 10,000 to about 100,000,000 members. In yet another embodiment, the library includes from about 100,000 to about 100,000,000 members. In a further embodiment, the library includes from about 1,000,000 to about 100,000,000 members. In another embodiment, the library includes from about 10,000,000 to about 100,000,000 members. In yet another embodiment, the library includes more than 100 members.

The members of the library may be part of a mixture or may be isolated from each other. In one example, the members of the library are part of a mixture that optionally includes other components. For example, at least two polypeptides are present in a volume of cell-culture broth. In another example, the members of the library are each expressed separately and are optionally isolated. The isolated polypeptides may optionally be contained in a multi-well container, in which each well contains a different type of polypeptide. In another example, the members of the library are each expressed as fusions to a yeast or bacteria cell or phage or viral particle.

As used herein, the term "polymeric modifying group" is a modifying group that includes at least one polymeric moiety (polymer). The polymeric modifying group added to a polypeptide can alter a property of such polypeptide, for example, its bioavailability, biological activity or its half-life in the body. Exemplary polymers include water soluble and water insoluble polymers. A polymeric modifying group can be linear or branched and can include one or more independently selected polymeric moieties, such as poly(alkylene glycol) and derivatives thereof. In one example, the polymer is non-naturally occurring. In an exemplary embodiment, the polymeric modifying group includes a water-soluble polymer, e.g., poly(ethylene glycol) and derivatived thereof (PEG, m-PEG), poly(propylene glycol) and derivatives thereof (PPG, m-PPG) and the like. In a preferred embodiment, the poly(ethylene glycol) or poly(propylene glycol) has a molecular weight that is essentially homodisperse. In one embodiment the polymeric modifying group is not a naturally occurring polysaccharide.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

The term "Fc-fusion protein", as used herein, is meant to encompass proteins, in particular therapeutic proteins, comprising an immunoglobulin-derived moiety, which will be called herein the "Fc-moiety", and a moiety derived from a second, non-immunoglobulin protein, which will be called herein the "therapeutic moiety", irrespective of whether or not treatment of disease is intended.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g, multivalent agents. Therapeutic moiety also includes proteins and constructs that include proteins.

As used herein, "anti-tumor drug" means any agent useful to combat cancer including.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

As used herein, "a radioactive agent" includes any radioisotope that is effective in diagnosing or destroying a tumor. Examples include, but are not limited to, indium-111, cobalt-60, fluorine-18, copper-64, copper-67, lutetium-177, or technicium-99m. Additionally, naturally occurring radioactive elements such as uranium, radium, and thorium, which typically represent mixtures of radioisotopes, are suitable examples of a radioactive agent. The metal ions are typically chelated with an organic chelating moiety. The radioactive agent or radionuclide can be a component of an imaging agent.

Near-infrared dyes can also be conjugated using standard chemistries for optical imaging applications. "Near infrared" refers to radiation in the portion of the electromagnetic spectrum adjacent to that portion associated with visible light, for example, from about 0.7 µm to about 1 µm. The near infrared dye may include, for example, a cyanine or indocyanine derivative such as Cy5.5. The infrared dye may also include phosphoramidite dyes, for example, IRDye® 800 (LI-COR® Biosciecnes).

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein. Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997). These metal binding agents can be used to bind a metal ion detectable in an imaging modality.

As used herein, "pharmaceutically acceptable carrier" includes any material, which when combined with the conjugate retains the conjugates' activity and is non-reactive with the subject's immune systems. "Pharmaceutically acceptable carrier" includes solids and liquids, such as vehicles, diluents and solvents. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering" means oral administration, administration as a suppository, topical contact, intravenous, intraperitoneal, intramuscular, intrathecal, intralesional, or subcutaneous administration, administration by inhalation, or the implantation of a slow-release device, e.g., a mini-osmotic pump, to the subject. Adminsitration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in a subject (e.g., human) that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any grammatically equivalent term means the amount that, when administered to an animal or human for treating a disease, is sufficient to effect treatment for that disease. An effective amount can also refer to the amount necessary to cause a cellular response, including for example, apoptosis, cell cycle initiation, and/or signal transduction.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are intended to be encompassed within the scope of the present invention.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

III. The Embodiments

The Variants

The present invention provides an hHGF polypeptide including at least one amino acid in at least one position in which this amino acid is not found in the parent hHGF polypeptide (wild type). The invention encompasses variants of all isoforms of hHGF including, but not limited to isoforms 1 and 3. Isoform 3 (NCBI accession NP_001010932) includes the five amino acid deletion (SFLPS) underlined in SEQ. ID. NO.:1 (isoform 1), below.

In an exemplary embodiment, the invention provides a variant of SEQ. ID. NO.: 1 having at least one amino acid substitution.

In an exemplary embodiment, the variant is an isolated variant. Furthermore, in various embodiments, the variant exhibits at least one desirable characteristic not present in the present polypeptide. Exemplary characteristics include, but are not limited to, an increase in affinity for the Met receptor, an increase in thermal stability, increase or decrease in conformational flexibility and an increased agonist or antagonistic activity towards the Met receptor. As will be appreciated by those of skill in the art, the variant may exhibit any combination of two or more of these improved characteristics.

In an exemplary embodiment, the polypeptide variant is an antagonist for the Met receptor. In various embodiments, the variant is an agonist of the Met receptor In an exemplary embodiment, the invention provides an hHGF polypeptide variant having a sequence which is a member selected from SEQ. ID. NO.:2-22.

An exemplary parent polypeptide is wild type HGF isoform 1 (HGF NCBI accession NP_000592) (SEQ. ID NO.: 1)

```
MWVTKLLPAL LLQHVLLHLL LLPIAIPYAE GQRKRRNTIH

EFKKSAKTTL IKIDPALKIKTKKVNTADQC ANRCTRNKGL

PFTCKAFVFD KARKQCLWFP FNSMSSGVKK

EFGHEFDLYENKDYIRNCII GKGRSYKGTV SITKSGIKCQ

PWSSMIPHEH SFLPSSYRGK DLQENYCRNPRGEEGGPWCF

TSNPEVRYEV CDIPQCSEVE CMTCNGESYR GLMDHTESGK

ICQRWDHQTPHRHKFLPERY PDKGFDDNYC RNPDGQPRPW

CYTLDPHTRW EYCAIKTCAD NTMNDTDVPLETTECIQGQG

EGYRGTVNTI WNGIPCQRWD SQYPHEHDMT PENFKCKDLR

ENYCRNPDGSESPWCFTTDP NIRVGYCSQI PNCDMSHGQD

CYRGNGKNYM GNLSQTRSGL TCSMWDKNMEDLHRHIFWEP

DASKLNENYC RNPDDDAHGP WCYTGNPLIP WDYCPISRCE

GDTTPTIVNLDHPVISCAKT KQLRVVNGIP TRTNIGWMVS

LRYRNKHICG GSLIKESWVL TARQCFPSRDLKDYEAWLGI

HDVHGRGDEK CKQVLNVSQL VYGPEGSDLV LMKLARPAVL

DDFVSTIDLPNYGCTIPEKT SCSVYGWGYT GLINYDGLLR

VAHLYIMGNE KCSQHHRGKV TLNESEICAGAEKIGSGPCE

GDYGGPLVCE QHKMRMVLGV IVPGRGCAIP NRPGIFVRVA

YYAKWIHKIILTYKVPQS
```

In SEQ. ID. NO.: 1, the signal peptide comprises amino acids 1-31. The N-terminal domain comprises amino acids 39-122. The Kringle 1 domain comprises amino acids 126-207; Kringle 2 comprises amino acids 208-289; Kringle 3 comprises amino acids 302-384; Kringle 4 comprises amino acids 388-470. The serine protease-like domain comprises 495-719.

In an exemplary embodiment, variants of the invention have a sequence identity with the parent polypeptide of at least about 80%, at least about 85%, at least about 90%, at least about 95% or at least about 96%, 97%, 98% or 99%. In various embodiments, the variants of the invention have a sequence identity with the parent poly peptide of at least about 99.2%, at least about 99.4%, at least about 99.6% or at least about 99.8%.

In an exemplary embodiment, the positions of SEQ. ID. NO.: 1, which are mutated include one or more of 62, 64, 77, 95, 125, 127, 130, 132, 137, 142, 148, 154, 170, 173 and 193. As those of skill will realize, any combination of these positions can be mutated. In various embodiments, analogous positions of isoform 3 are mutated.

In an exemplary embodiment, an amino acid of the parent polypeptide is altered from K to a member selected from E, N and R. In an exemplary embodiment, an amino acid in the parent polypeptide is altered from Q to R. In an exemplary embodiment, an amino acid in the parent polypeptide is altered from I to a member selected from T and V. In an exemplary embodiment, an amino acid of the parent polypeptide is altered from N to D. In some embodiments the D can be reverted back to N of the parent polypeptide.

In various embodiments, the amino acid at position 42 is an F or a C. In various embodiments, the amino acid at position 62 is changed from K, found in the wild type parent polypeptide to E. In various embodiments, position 64 is a V or an A. In various embodiments, position 77 is an N or an S. In various embodiments, the amino acid at position 95 is a Q, or anR. In various embodiments, the amino acid at position 125 is changed from I, found in the wild type parent polypeptide, to T. In various embodiments, the amino acid at position 127 can be D, N, K, R or A. In various embodiments, the amino acid at position 130 is changed from I to V. In various embodiments, the amino acid at position 132 is changed from a K, to an N or R. In various embodiments, the amino acid at position 137 is a K or an R. In various embodiments, the amino acid of position 154 is an S or an A. In various embodiments, the amino acid at position 170 is a K, or an E. In various embodiments, the amino acid at position 173 is a Q or a R. In various embodiments, the amino acid at position 193 is a N, or a D. In various embodiments, the amino acid at position 42 is an F or a C. In various embodiments, the amino acid at position 96 is a C or an R. As those of skill will appreciate, any combination of these changes, as well as any combination of those set forth in the tables that follow, can be present in a polypeptide variant of the invention.

Tables 1, 2 and 3 show exemplary mutations of the invention.

TABLE 1

|  | N-domain | | Linker | | K1 domain | | | | | |
| --- | --- | --- | --- | --- | --- | --- | --- | --- | --- | --- |
|  | 62 | 95 | 125 | 127 | 130 | 132 | 137 | 170 | 173 | 193 |
| hHGF | K | Q | I | N | I | K | K | K | Q | N |
| Consensus | E | R | T | D | V | N | R | E | R | D |
| M2.1 | E | | | D | | | R | E | | D |
| M2.2 | E | R | | D | | N | R | E | R | D |

TABLE 2

Individual sequence mutations of NK1 mutants isolated from the third round of directed evolution. SEQ ID NO: 1 is wild-type; only differences from wild-type sequence are shown in SEQ ID NOs: 2-22; blank spaces mean the wild-type hHGF residue is retained.

| SEQ ID | Isofm | bp | AA | 28 | 30 | 33 | 37 | 38 | 42 | 44 | 48 | 58 | 62 | 64 | 65 | 75 | 77 | 82 | 95 |
|---|---|---|---|---|---|---|---|---|---|---|---|---|---|---|---|---|---|---|---|
| 1 | | | | Y | E | R | N | T | F | K | T | K | K | V | N | T | N | F | Q |
| 2 | 1 | 15 | 12 | | | | | | | | | R | E | A | | | S | | R |
| 3 | 1 | 21 | 15 | | | | | | | | | | E | A | | I | | | R |
| 4 | 1 | 16 | 14 | | | | | | | | | | E | A | | | S | | R |
| 5 | 1 | 18 | 15 | | | K | G | | | | | | E | A | D | | S | | |
| 6 | 1 | 19 | 15 | | | | | | | | A | R | E | A | | | S | | R |
| 7 | 1 | 20 | 15 | | | | | | | | | | E | A | | | S | | R |
| 8 | 1 | 16 | 13 | | | | | | | | | | E | A | | I | | | |
| 9 | 1 | 28 | 20 | | | | | D | A | C | R | | E | A | | | | S | R |
| 10 | 1 | 14 | 12 | | | | G | | | | | | E | | | | S | | R |
| 11 | 1 | 17 | 15 | H | | | | | | | | | E | A | | | S | | R |

| SED ID No | 96 | 98 | 101 | 123 | 125 | 127 | 130 | 132 | 135 | 137 | 142 | 148 | 154 | 168 | 170 | 173 | 181 | 190 | 193 |
|---|---|---|---|---|---|---|---|---|---|---|---|---|---|---|---|---|---|---|---|
| 1 | C | W | F | D | I | N | I | K | S | K | I | K | S | R | K | Q | R | F | N |
| 2 | | | | | D | | | | | R | | | A | | E | R | | Y | D |
| 3 | | | V | | T | | V | N | | R | T | | A | | E | R | | Y | D |
| 4 | | | | | D | V | N | | R | | | E | A | | E | R | | Y | D |
| 5 | | | | | D | V | N | | R | V | | | | | E | R | | Y | D |
| 6 | | | | | D | V | N | | R | | | E | | | E | | W | Y | D |
| 7 | | | | | T | V | N | | R | | | E | A | Q | E | R | | Y | D |
| 8 | | | A | | D | | R | N | R | | | E | | | E | R | | Y | D |
| 9 | R | R | | | T | V | N | | R | T | | | A | | E | R | W | | D |
| 10 | | | | | D | | R | | R | | | | A | | E | R | | Y | D |
| 11 | | | | | T | V | N | | R | T | | | A | | E | R | | Y | D | bp: number of base pair mutations
AA: number of amino acid mutations

TABLE 3

Individual sequence mutations of NK1 mutants isolated from the third round of directed evolution. SEQ ID NO: 1 is wil-type; only differences from wild-type sequence are shown in SEQ ID NOs: 2-22.

| | Isofm | bp | AA | 30 | 33 | 46 | 58 | 62 | 64 | 65 | 75 | 77 | 78 | 79 | 95 | 101 |
|---|---|---|---|---|---|---|---|---|---|---|---|---|---|---|---|---|
| 1 | | | | E | R | A | K | K | V | N | T | N | K | G | Q | F |
| 12 | 1 | 17 | 13 | | | | | E | A | | | S | R | | | |
| 13 | 1 | 16 | 11 | | | | | E | A | | | | | | R | |
| 14 | 1 | 20 | 17 | | | V | | E | A | | | S | | | R | V |
| 15 | 1 | 18 | 13 | | | | | E | A | | | S | | | R | |
| 16 | 1 | 17 | 13 | | | | R | E | A | | | S | R | | R | |
| 17 | 1 | 21 | 16 | | | | | E | A | | | S | R | R | R | |
| 18 | 1 | 16 | 14 | | | | | E | A | | | S | | | R | |
| 19 | 1 | 14 | 9 | | | | | | | D | | | | | R | |
| 20 | 1 | 24 | 16 | | | G | | R | E | A | | | S | | | R |
| 21 | 1 | 21 | 15 | K | | | | R | E | | | I | | | R | |
| 22 | 1 | 14 | 12 | | | G | | E | | | | S | | | R | |

| | 112 | 123 | 127 | 130 | 132 | 135 | 137 | 142 | 148 | 154 | 166 | 170 | 173 | 181 | 190 | 193 |
|---|---|---|---|---|---|---|---|---|---|---|---|---|---|---|---|---|
| 1 | F | D | N | I | K | S | K | I | K | S | S | K | Q | R | F | N |
| 12 | | D | | N | | R | V | | A | | | E | R | | Y | D |
| 13 | | D | V | N | | R | | | | | | E | R | | Y | D |
| 14 | S | D | V | N | | R | T | | A | | | E | R | | Y | D |
| 15 | | D | V | N | | R | | | | | | E | R | W | Y | D |
| 16 | | D | | N | | R | | | | | | E | R | | Y | D |
| 17 | | D | | | | R | V | E | A | N | | E | R | | Y | D |
| 18 | | D | V | N | | R | | E | A | | | E | R | | Y | D |
| 19 | | D | | N | | R | | | | | | E | R | | Y | D |
| 20 | A | D | | R | N | R | | | A | | | E | R | | Y | D |
| 21 | A | D | | R | N | R | | | A | | | E | R | | Y | D |
| 22 | | D | | N | | R | | | A | | | E | R | | Y | D | bp: number of base pair mutations
AA: number of amino acid mutations

Conjugates

The present invention provides conjugates of the variants of the invention with one or more conjugation partner. Exemplary conjugation partners include polymers, targeting agents, therapeutic agents, cytotoxic agents, chelating agents and detectable agents. Those of skill will recognize that there is overlap between these non-limiting agent categories.

The conjugation partner or "modifying group" can be any conjugatable moiety. Exemplary modifying groups are discussed below. The modifying groups can be selected for their ability to alter the properties (e.g., biological or physicochemical properties) of a given polypeptide. Exemplary polypeptide properties that may be altered by the use of modifying groups include, but are not limited to, pharmacokinetics, pharmacodynamics, metabolic stability, biodistribution, water solubility, lipophilicity, tissue targeting capabilities and the therapeutic activity profile. Modifying groups are useful for the modification of polypeptides of use in diagnostic applications or in in vitro biological assay systems.

In some embodiments, a HGF variant of the instant invention is combined with an Fc moiety. The Fc-moiety may be derived from a human or animal immunoglobulin (Ig) that is preferably an IgG. The IgG may be an IgG1, IgG2, IgG3 or IgG4. It is also preferred that the Fc-moiety is derived from the heavy chain of an immunoglobulin, preferably an IgG. More preferably, the Fc-moiety comprises a portion, such as e.g. a domain, of an immunoglobulin heavy chain constant region. Such Ig constant region preferably comprises at least one Ig constant domain selected from any of the hinge, CH2, CH3 domain, or any combination thereof. It is preferred that the Fc-moiety comprises at least a CH2 and CH3 domain. It is further preferred that the Fc-moiety comprises the IgG hinge region, the CH2 and the CH3 domain.

Fc domains of the IgG1 subclass are often used as the Fc moiety, because IgG1 has the longest serum half-life of any of the serum proteins. Lengthy serum half-life can be a desirable protein characteristic for animal studies and potential human therapeutic use. In addition, the IgG1 subclass possesses the strongest ability to carry out antibody mediated effector functions.

The primary effector function that may be most useful in a fusion protein is the ability for an IgG1 antibody to mediate antibody dependent cellular cytotoxicity. On the other hand, this could be an undesirable function for a fusion protein that functions primarily as an antagonist. Several of the specific amino acid residues that are important for antibody constant region-mediated activity in the IgG1 subclass have been identified. Inclusion or exclusion of these specific amino acids therefore allows for inclusion or exclusion of specific immunoglobulin constant region-mediated activity.

In accordance with the present invention, the Fc-moiety may also be modified in order to modulate effector functions. For instance, the following Fc mutations, according to EU index positions (Kabat et al., 1991), can be introduced if the Fc-moiety is derived from IgG1: T250Q/M428L; M252Y/S254T/T256E+H433K/N434F; E233P/L234V/L235A/A4236+A327G/A330S/P331S; E333A; K322A.

Further Fc mutations may e.g. be the substitutions at EU index positions selected from 330, 331 234, or 235, or combinations thereof. An amino acid substitution at EU index position 297 located in the CH2 domain may also be introduced into the Fc-moiety in the context of the present invention, eliminating a potential site of N-linked carbohydrate attachment. The cysteine residue at EU index position 220 may also be replaced.

The Fc-fusion protein of the invention may be a monomer or dimer. The Fc-fusion protein may also be a "pseudo-dimer", containing a dimeric Fc-moiety (e.g. a dimer of two disulfide-bridged hinge-CH2-CH3 constructs), of which only one is fused to a therapeutic moiety.

The Fc-fusion protein may be a heterodimer, containing two different therapeutic moieties, or a homodimer, containing two copies of a single therapeutic moiety.

In some embodiments, the in vivo half-life of the HGF variants can be enhanced with polyethylene glycol (PEG) moieties. Chemical modification of polypeptides with PEG (PEGylation) increases their molecular size and typically decreases surface- and functional group-accessibility, each of which are dependent on the number and size of the PEG moieties attached to the polypeptide. Frequently, this modification results in an improvement of plasma half-live and in proteolytic-stability, as well as a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). For example, PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)). Thus, in another embodiment, the in vivo half-life of a polypeptide derivatized with a PEG moiety by a method of the invention is increased relative to the in vivo half-life of the non-derivatized parent polypeptide.

The increase in polypeptide in vivo half-life is best expressed as a range of percent increase relative to the parent polypeptide. The lower end of the range of percent increase is about 40%, about 60%, about 80%, about 100%, about 150% or about 200%. The upper end of the range is about 60%, about 80%, about 100%, about 150%, or more than about 250%.

Many water-soluble polymers are known to those of skill in the art and are useful in practicing the present invention. The term water-soluble polymer encompasses species such as saccharides (e.g., dextran, amylose, hyalouronic acid, poly(sialic acid), heparans, heparins, etc.); poly(amino acids), e.g., poly(aspartic acid) and poly(glutamic acid); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached. See, for example, Harris, *Macronol. Chem. Phys. C*25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002).

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic polypeptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate)polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics and polyvinylphenol and copolymers thereof.

Representative biodegradable polymers of use in the conjugates of the invention include, but are not limited to, polylactides, polyglycolides and copolymers thereof, poly (ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

Exemplary resorbable polymers include, for example, synthetically produced resorbable block copolymers of poly (α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301-1316 (1987); and Cohn et al., *J Biomed. Mater. Res.* 22: 993-1009 (1988).

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

In another embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The present invention also provides conjugates analogous to those described above in which the polypeptide is conjugated to a therapeutic moiety, diagnostic moiety, targeting moiety, toxin moiety or the like. Each of the above-recited moieties can be a small molecule, natural polymer (e.g., polypeptide) or a synthetic polymer.

In various embodiments, the variant is conjugated to a component of a matrix for tissue regeneration. Exemplary matrices are known in the art and it is within the ability of a skilled worker to select and modify an appropriate matrix with an HGF variant of the invention. The HGF variants of the invention are generally of use in regenerative medicine applications, including the regeneration of, e.g., liver, muscle, nerve and cardiac tissue. See, for example, Isobe et al., Hepatocyte growth factor: Effects on immune-mediated heart diseases. *Trends Cardiovasc Med.,* 16 (6) pp. 188-93 (2006); Anderson et al., The role of cytoprotective cytokines in cardiac ischemia/reperfusion injury. *Journal of Surgical Research,* 148 (2) pp. 164-71 (2008); Maulik et al., Growth factors and cell therapy in myocardial regeneration. *Journal of Molecular and Cellular Cardiology,* 44 (2) pp. 219-27 (2008); Chen et al., In vivo hepatocyte growth factor gene transfer reduces myocardial ischemia-reperfusion injury through its multiple actions. *Journal Cardiac Failure,* 13 (10) pp. 874-83 (2007); Kondo et al., Treatment of acute myocardial infarction by hepatocyte growth factor gene transfer: The first demonstration of myocardial transfer of a "functional" gene using ultrasonic microbubble destruction. *Journal of the American College of Cardiology,* 44 (3) pp. 644-53 (2004); Schirmer et al., Stimulation of collateral artery growth: travelling further down the road to clinical application. *Heart,* 95 (3) pp. 191-197 (2009); Zhu et al., Transplantation of adipose-derived stem cells overexpressing hHGF into cardiac tissue. Biochemical and Biophysical Research Communication, 379 (4) pp. 1084-90 (2009); Carlsson et al., Quantitative MR measurements of regional and global left ventricular function and strain after intramyocardial transfer of VM202 into infarcted swine myocardium. *Am. J. Physiol. Heart Circ. Physiol.,* 295 (2) pp. H522-32 (2008); Schuldiner et al., Effects of eight growth factors on the differentiation of cells derived from human embryonic cells. PNAS, 97 (21) pp. 11307-11312 (2000); Cassano et al., Magic-Factor 1, a Partial Agonist of Met, Induces Muscle Hypertrophy by Protecting Myogenic Progenitors from Apoptosis. PloS One vol. 3 (9) pp. 1-13 (2008); Linke et al., Stems cells in the dog heart are self-renewing clonogenic, and multipotent and regenerate infarcted myocardium, improving cardiac function. PNAS vol. 102 (25) pp. 8966-8971 (2005); Takahara et al., Metron Factor-1 Prevents Liver Injury without Promoting Tumor Growth and Metastasis, *Hepatology,* 47 (6) pp. 2010-2025 (2008); Neuss et al., Functional Expression of HGF and HGF Receptor/c-met in Adult Human Mesenchymal Stem Cells Suggest a Role in Cell Mobilization, Tissue Repair, and Wound Healing. *Stem Cells,* 22 pp. 405-414 (2004).

In a still further embodiment, the invention provides conjugates that localize selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), IL-2 and IFN-α.

In another embodiment, the invention provides a conjugate between a polypeptide of the invention and a therapeutic moiety. Therapeutic moieties, which are useful in practicing the instant invention include drugs from a broad range of drug classes having a variety of pharmacological activities. Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

Classes of useful therapeutic moieties include, for example, antineoplastic drugs (e.g., antiandrogens (e.g., leuprolide or flutamide), cytocidal agents (e.g., adriamycin, doxorubicin, taxol, cyclophosphamide, busulfan, cisplatin, β-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanamycin, mytansin, CC-1065, the duocarmycins, Chlicheamycin and related structures and analogues thereof.

The therapeutic moiety can also be a hormone (e.g., medroxyprogesterone, estradiol, leuprolide, megestrol, octreotide or somatostatin); endocrine modulating drugs (e.g., contraceptives (e.g., ethinodiol, ethinyl estradiol, norethindrone, mestranol, desogestrel, medroxyprogesterone). Of use in various embodiments of the invention are conjugates with estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

In various embodiments, the conjugate is formed by reaction between a reactive amino acid and a reactive conjugation partner for the reactive amino acid. Both the reactive amino acid and the reactive conjugation partner include within their framework one or more reactive functional group. One of the two binding species may include a "leaving group" (or activating group) refers to those moieties, which are easily displaced in enzyme-regulated nucleophilic substitution reactions or alternatively, are replaced in a chemical reaction utilizing a nucleophilic reaction partner (e.g., an amino acid moiety carrying a sufhydryl group). It is within the abilities of a skilled person to select a suitable leaving group for each type of reaction. Many activated sugars are known in the art. See, for example, Vocadlo et al., In CARBOHYDRATE CHEMISTRY AND BIOLOGY, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

In various embodiments, the amino acid substitution, which is the variant (or a variant) of naturally occurring HGF, is the locus for attachment of the conjugation partner, e.g., a side-chain amino acid, e.g., cysteine, lysine, serine, etc.

Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Reactive Functional Groups

Useful reactive functional groups on a reactive amino acid or reactive conjugation partner include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

The group linking the polypeptide and conjugation partner can also be a cross-linking group, e.g., a zero- or higher-order cross-linking group (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

Exemplary conjugation partners attached to the polypeptides of the invention include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, $Sle_x$, mannose, mannose-6-phosphate, Sialyl Lewis X, FGF, VFGF, proteins, chondroitin, keratan, dermatan, albumin, integrins, antennary oligosaccharides, peptides and the like.

In addition to covalent attachments, the polypeptides of the instant invention can be attached onto the surface of a biomaterial through non-covalent interactions. Non covalent protein incorporation can be done, for example, through encapsulation or absorption. Attachment of the polypeptides of the instant invention to a biomaterial may be mediated through heparin. In some embodiments, the polypeptides of the instant invention are attached to a heparin-alginate polymer and alginate as described in Harada et al., J. Clin. Invest. (1994) 94:623-630; Laham et al., Circulation (1999) 1865-1871 and references cited therein. In other embodiments, the polypeptides of the instant invention are attached to a collagen based biomaterial.

Imaging Agents

An exemplary conjugate of the invention is an imaging agent comprising a variant of the invention and a detectable moiety, which is detectable in an imaging modality. There is a critical need for molecular imaging probes that will specifically target Met receptors in living subjects and allow noninvasive characterization of tumors for patient-specific cancer treatment and disease management. The ability to detect Met-expressing tumors through non-invasive imaging could also serve as an indicator of metastatic risk.

Exemplary imaging modalities in which the conjugates of the invention find use include, without limitation, positron emission tomography (PET) in which a variant of the invention is tagged with a positron emitting isotope. Typical isotopes include $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, with $^{18}F$ being the most clinically utilized. The variants can also be incorporated into ultrasound agents, magnetic resonance imaging agents, X-ray agents, CT agents, gamma camera scintigraphy agents and fluorescent imaging agents. Additional detectable moieties and methods of imaging are set forth in the Methods section hereinbelow.

Compared to other tumor targets, such as integrin receptors, the development of Met-based imaging agents has been extremely limited. Thus far, a few Met-specific monoclonal antibodies have been radiolabeled and used to image Met-expressing tumors in mouse models. One limitation of this approach is that intact antibodies must be allowed to clear from the body for several days after injection before imaging studies can be performed or high background signals will result; this limits the radioisotopes that can be used for imaging to those with long half-lives (e.g., $^{125}I$) Moreover, the antibodies in these imaging studies were Met-receptor agonists, which could potentially induce Met receptor activation. To address these issues, a Met-binding Fab antibody fragment and a Met-binding peptide were both identified from phage-displayed libraries. Radiolabeled versions of these Met-targeting agents were shown to image tumors in living subjects; however tumor uptake was low, possibly due to the weak Met receptor binding affinity of these probes. These studies highlight that there is substantial room for improvement and further probe development.

In an exemplary embodiment, the conjugation partner is attached to a polypeptide variant of the invention via a linkage that is cleaved under selected conditions. Exemplary conditions include, but are not limited to, a selected pH (e.g., stomach, intestine, endocytotic vacuole), the presence of an active enzyme (e.g, esterase, reductase, oxidase), light, heat and the like. Many cleavable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989).

Pharmaceutical Compositions

Polypeptides and their conjugates of the invention have a broad range of pharmaceutical applications.

Thus, in another aspect, the invention provides a pharmaceutical composition including at least one polypeptide or polypeptide conjugate of the invention and a pharmaceutically acceptable diluent, carrier, vehicle, additive or combinations thereof. Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable matrices, such as microspheres (e.g., polylactate polyglycolate), may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered subcutaneously or parenterally, e.g., intravenously. Thus, the invention provides compositions for parenteral administration, which include the compound dissolved or suspended in an acceptable carrier, preferably an aqueous carrier, e.g., water, buffered water, saline, PBS and the like. The compositions may also contain detergents such as Tween 20 and Tween 80; stabilizers such as mannitol, sorbitol, sucrose, and trehalose; and preservatives such as EDTA and meta-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al.,

*Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}I$, $^{14}C$, or tritium.

Antibodies and Nucleic Acids

In various embodiments, the invention provides an isolated nucleic acid encoding a polypeptide variant according to any of the embodiments set forth hereinabove. In various embodiments, the invention provides a nucleic acid complementary to this nucleic acid.

In various embodiments, the invention provides an expression vector including a nucleic acid encoding a polypeptide variant according to any of the embodiments set forth hereinabove operatively linked to a promoter.

In various embodiments, the invention provides an antibody capable of specifically binding to a polypeptide variant of the invention. Also provided is an isolated nucleic acid encoding this antibody, an expression system encoding this antibody in which the nucleic acid encoding the antibody is operatively linked to a promoter. A cell expressing the antibody is also provided. In various embodiments, the invention provides an expression vector including a nucleic acid encoding a polypeptide variant according to any of the embodiments set forth hereinabove.

Libraries

Also provided in various embodiments is a library of variant hHGF polypeptides comprising a plurality of different members, wherein each member of the library corresponds to a common parent polypeptide hHGF and wherein each member of the library comprises an amino acid at a position at which the amino acid is not found in the parent polypeptide.

IV. Methods

Chemical Synthesis

Polypeptide variants of the invention may be prepared using conventional step-wise solution or solid phase synthesis (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the peptides of the invention may be prepared by way of segment condensation, as described, for example, in Liu et al., 1996, Tetrahedron Lett. 37(7)933 936; Baca, et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334). Segment condensation is a particularly useful method for synthesizing embodiments containing internal glycine residues. Other methods useful for synthesizing the peptides of the invention are described in Nakagawa et al., 1985, J. Am. Chem. Soc. 107:7087-7092. Polypeptide variants containing N- and/or C-terminal blocking groups can be prepared using standard techniques of organic chemistry. For example, methods for acylating the N-terminus of a peptide or amidating or esterifying the C-terminus of a peptide are well-known in the art. Modes of carrying other modifications at the N- and/or C-terminus will be apparent to those of skill in the art, as will modes of protecting any side-chain functionalities as may be necessary to attach terminal blocking groups. Pharmaceutically acceptable salts (counter ions) can be conveniently prepared by ion-exchange chromatography or other methods as are well known in the art.

Compounds of the invention which are in the form of tandem multimers can be conveniently synthesized by adding the linker(s) to the peptide chain at the appropriate step in the synthesis. Alternatively, the helical segments can be synthesized and each segment reacted with the linker. Of course, the actual method of synthesis will depend on the composition of the linker. Suitable protecting schemes and chemistries are well known, and will be apparent to those of skill in the art.

Compounds of the invention which are in the form of branched networks can be conveniently synthesized using the trimeric and tetrameric resins and chemistries described in Tam, 1988, Proc. Natl. Acad. Sci. USA 85:5409-5413 and Demoor et al., 1996, Eur. J. Biochem. 239:74-84. Modifying the synthetic resins and strategies to synthesize branched networks of higher or lower order, or which contain combinations of different core peptide helical segments, is well within the capabilities of those of skill in the art of peptide chemistry and/or organic chemistry. Formation of disulfide linkages, if desired, is generally conducted in the presence of mild oxidizing agents.

Chemical oxidizing agents may be used, or the compounds may simply be exposed to atmospheric oxygen to effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, Ill.;

Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Hely. Chim. Acta 63:899-915. A method conducted on solid supports is described by Albericio, 1985, Int. J. Peptide Protein Res. 26:92-97. Any of these methods may be used to form disulfide linkages in the peptides of the invention.

Acquisition of Polypeptide Coding Sequences

General Recombinant Technology

The creation of mutant polypeptides, which incorporate an O-linked glycosylation sequence of the invention can be accomplished by altering the amino acid sequence of a corresponding parent polypeptide, by either mutation or by full chemical synthesis of the polypeptide. The polypeptide amino acid sequence is preferably altered through changes at the DNA level, particularly by mutating the DNA sequence encoding the polypeptide at preselected bases to generate codons that will translate into the desired amino acids. The DNA mutation(s) are preferably made using methods known in the art.

This invention relies on routine techniques in the field of recombinant genetics. Basic texts disclosing the general methods of use in this invention include Sambrook and Russell, Molecular Cloning, A Laboratory Manual (3rd ed. 2001); Kriegler, *Gene Transfer and Expression: A Laboratory Manual* (1990); and Ausubel et al., eds., *Current Protocols in Molecular Biology* (1994).

Nucleic acid sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Entire genes can also be chemically synthesized. Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type polypeptide genes, polynucleotide encoding mutant polypeptides, and synthetic oligonucleotides can be verified after cloning using, e.g., the chain termination method for sequencing double-stranded templates of Wallace et al., *Gene* 16: 21-26 (1981).

In an exemplary embodiment, the glycosylation sequence is added by shuffling polynucleotides. Polynucleotides encoding a candidate polypeptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

Cloning and Subcloning of a Wild-Type Peptide Coding Sequence

Numerous polynucleotide sequences encoding wild-type polypeptides have been determined and are available from a commercial supplier, e.g., human growth hormone, e.g., GenBank Accession Nos. NM 000515, NM 002059, NM 022556, NM 022557, NM 022558, NM 022559, NM 022560, NM 022561, and NM 022562.

The rapid progress in the studies of human genome has made possible a cloning approach where a human DNA sequence database can be searched for any gene segment that has a certain percentage of sequence homology to a known nucleotide sequence, such as one encoding a previously identified polypeptide. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a polypeptide can be isolated from a human cDNA or genomic DNA library using standard cloning techniques such as polymerase chain reaction (PCR), where homology-based primers can often be derived from a known nucleic acid sequence encoding a polypeptide. Most commonly used techniques for this purpose are described in standard texts, e.g., Sambrook and Russell, supra.

cDNA libraries suitable for obtaining a coding sequence for a wild-type polypeptide may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full-length polynucleotide sequence encoding the wild-type polypeptide from the cDNA library. A general description of appropriate procedures can be found in Sambrook and Russell, supra.

A similar procedure can be followed to obtain a full length sequence encoding a wild-type polypeptide, e.g., any one of the GenBank Accession Nos mentioned above, from a human genomic library. Human genomic libraries are commercially available or can be constructed according to various art-recognized methods. In general, to construct a genomic library, the DNA is first extracted from an tissue where a polypeptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, PCR Technology, CRC Press Inc. 1994) to amplify a segment of nucleotide sequence from a cDNA or genomic library.

Using the amplified segment as a probe, the full-length nucleic acid encoding a wild-type polypeptide is obtained.

Upon acquiring a nucleic acid sequence encoding a wild-type polypeptide, the coding sequence can be subcloned into a vector, for instance, an expression vector, so that a recombinant wild-type polypeptide can be produced from the resulting construct. Further modifications to the wild-type polypeptide coding sequence, e.g., nucleotide substitutions, may be subsequently made to alter the characteristics of the molecule.

Introducing Mutations into a Polypeptide Sequence

From an encoding polynucleotide sequence, the amino acid sequence of a wild-type polypeptide can be determined. Subsequently, this amino acid sequence may be modified to alter the protein's glycosylation pattern, by introducing additional glycosylation sequence(s) at various locations in the amino acid sequence.

A variety of mutation-generating protocols are established and described in the art. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortie, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

Modification of Nucleic Acids for Preferred Codon Usage in a Host Organism

The polynucleotide sequence encoding a polypeptide variant can be further altered to coincide with the preferred codon usage of a particular host. For example, the preferred codon usage of one strain of bacterial cells can be used to derive a polynucleotide that encodes a polypeptide variant of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the polypeptide variant coding sequences are verified by sequencing and are then subcloned into an appropriate expression vector for recombinant production in the same manner as the wild-type polypeptides.

Expression of Mutant Polypeptides

Following sequence verification, the polypeptide variant of the present invention can be produced using routine techniques in the field of recombinant genetics, relying on the polynucleotide sequences encoding the polypeptide disclosed herein.

Expression Systems

To obtain high-level expression of a nucleic acid encoding a mutant polypeptide of the present invention, one typically subclones a polynucleotide encoding the mutant polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the mutant polypeptide in host cells. A typical expression cassette thus contains a promoter operably linked to the nucleic acid sequence encoding the mutant polypeptide and signals required for efficient polyadenylation of the transcript, ribosome binding sites, and translation termination. The nucleic acid sequence encoding the polypeptide is typically linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322-based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

In some exemplary embodiments the expression vector is chosen from pCWin1, pCWin2, pCWin2/MBP, pCWin2-MBP-SBD (pMS$_{39}$), and pCWin2-MBP-MCS-SBD (pMXS$_{39}$) as disclosed in co-owned U.S. patent application filed Apr. 9, 2004 which is incorporated herein by reference.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant polypeptide under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

When periplasmic expression of a recombinant protein (e.g., a hgh mutant of the present invention) is desired, the expression vector further comprises a sequence encoding a secretion signal, such as the E. coli OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., Gene 39: 247-254 (1985), U.S. Pat. Nos. 6,160,089 and 6,436,674.

As discussed above, a person skilled in the art will recognize that various conservative substitutions can be made to any wild-type or mutant polypeptide or its coding sequence while still retaining the biological activity of the polypeptide. Moreover, modifications of a polynucleotide coding sequence may also be made to accommodate preferred codon usage in a particular expression host without altering the resulting amino acid sequence.

Transfection Methods

Standard transfection methods are used to produce bacterial, mammalian, yeast or insect cell lines that express large quantities of the mutant polypeptide, which are then purified using standard techniques (see, e.g., Colley et al., J. Biol. Chem. 264: 17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132: 349-351 (1977); Clark-Curtiss & Curtiss, Methods in Enzymology 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the mutant polypeptide.

Detection of Expression of Mutant Polypeptides in Host Cells

After the expression vector is introduced into appropriate host cells, the transfected cells are cultured under conditions favoring expression of the mutant polypeptide. The cells are then screened for the expression of the recombinant polypeptide, which is subsequently recovered from the culture using standard techniques (see, e.g., Scopes, Protein Purification: Principles and Practice (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant polypeptide in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant polypeptide of the present invention (e.g., Harlow and Lane, Antibodies, A Laboratory Manual, Chapter 14, Cold Spring Harbor, 1988; Kohler and Milstein, Nature, 256: 495-497 (1975)). Such techniques require antibody preparation by selecting antibodies with high specificity against the mutant polypeptide or an antigenic portion thereof. The methods of raising polyclonal and monoclonal antibodies are well established and their descriptions can be found in the literature, see, e.g., Harlow and Lane, supra; Kohler and Milstein, Eur. J. Immunol., 6: 511-519 (1976). More detailed descriptions of preparing antibody against the mutant polypeptide of the present invention and conducting immunological assays detecting the mutant polypeptide are provided in a later section.

Purification of Recombinantly Produced Mutant Polypeptides

Once the expression of a recombinant mutant polypeptide in transfected host cells is confirmed, the host cells are then cultured in an appropriate scale for the purpose of purifying the recombinant polypeptide.

1. Purification from Bacteria

When the mutant polypeptides of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

For further description of purifying recombinant polypeptides from bacterial inclusion body, see, e.g., Patra et al., *Protein Expression and Purification* 18: 182-190 (2000).

The recombinant proteins present in the supernatant can be separated from the host proteins by standard separation techniques well known to those of skill in the art.

Immunoassays for Detection of Mutant Polypeptide Expression

To confirm the production of a recombinant mutant polypeptide, immunological assays may be useful to detect in a sample the expression of the polypeptide. Immunological assays are also useful for quantifying the expression level of the recombinant hormone. Antibodies against a mutant polypeptide are necessary for carrying out these immunological assays.

Production of Antibodies against Mutant Polypeptides

Methods for producing polyclonal and monoclonal antibodies that react specifically with an immunogen of interest are known to those of skill in the art (see, e.g., Coligan, *Current Protocols in Immunology* Wiley/Greene, N.Y., 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant polypeptide of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above. Monoclonal antibodies are obtained using various techniques familiar to those of skill in the art.

Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When desired, antibodies capable of specifically recognizing a mutant polypeptide of the present invention can be tested for their cross-reactivity against the wild-type polypeptide and thus distinguished from the antibodies against the wild-type protein. For instance, antisera obtained from an animal immunized with a mutant polypeptide can be run through a column on which a wild-type polypeptide is immobilized. The portion of the antisera that passes through the column recognizes only the mutant polypeptide and not the wild-type polypeptide. Similarly, monoclonal antibodies against a mutant polypeptide can also be screened for their exclusivity in recognizing only the mutant but not the wild-type polypeptide.

Polyclonal or monoclonal antibodies that specifically recognize only the mutant polypeptide of the present invention but not the wild-type polypeptide are useful for isolating the mutant protein from the wild-type protein, for example, by incubating a sample with a mutant peptide-specific polyclonal or monoclonal antibody immobilized on a solid support.

Methods of Treatment and Diagnosis

In various embodiments, the invention provides a method of preventing, ameliorating or treating a disease state, which can be treated by inhibiting Met. In these embodiments, the invention provides a method that comprises administering to a subject in need thereof an amount of a polypeptide variant Met inhibitor of the invention sufficient to prevent, ameliorate or treat the disease state. An exemplary disease state is cancer. The disclosed agonist variants can be useful for the promotion of cell growth, particularly for angiogenesis, and the treatment of cardiovascular, hepatic, musculoskeletal and neuronal diseases.

For example, in the adult, the HGF-Met pathway is involved in muscle regeneration following injury. Thus, the disclosed variants can find use in repairing muscle injuries, including for example, cardiac tissue regeneration following infarction.

The disclosed variants can be used, for example, be used to treat or prevent liver failure or disease caused by conditions including viral infection (such as by infection with a hepatitis virus, e.g. HAV, HBV or HCV), or other acute viral hepatitis, autoimmune chronic hepatitis, acute fatty liver of pregnancy, Budd-Chiari syndrome and veno-occlusive disease, hyperthermia, hypoxia, malignant infiltration, Reye's syndrome, sepsis, Wilson's disease and in transplant rejection.

The disclosed variants can be used to treat or prevent acute liver failure or disease induced by toxins, including a toxin selected from mushroom poisoning (e.g. Amanita phalloides), arsenic, carbon tetrachloride (or other chlorinated hydrocarbons), copper, ethanol, iron, methotrexate and phosphorus. A particular use of the polypeptides of the invention is in the treatment or prevention of liver damage caused by intoxication by N-acetyl-p-aminophenol (known commercially as paracetamol or acetaminophen).

Further, the disclosed variants can be useful in the treatment following kidney failure, supporting kidney maintenance and regeneration.

Because the polypeptide variants of the invention neutralize the activity of HGF, they can be used in various therapeutic applications. For example, certain polypeptide variants of the invention are useful in the prevention or treatment of hyperproliferative diseases or disorders, e.g., various forms of cancer.

In an exemplary embodiment, the invention provides a method of treating cancer in a subject in need of such treatment. The method includes administering to the subject a therapeutically effective amount of a polypeptide variant of the invention.

It is contemplated that the polypeptide variants of the invention can be used in the treatment of a variety of HGF responsive disorders, including, for example, HGF responsive tumor cells in lung cancer, breast cancer, colon cancer, prostate cancer, ovarian cancer, head and neck cancer, ovarian cancer, multiple myeloma, liver cancer, gastric cancer, esophageal cancer, kidney cancer, nasopharangeal cancer, pancreatic cancer, mesothelioma, melanoma and glioblastoma.

In exemplary embodiments, the cancer is a carcinoma, e.g., colorectal, squamous cell, hepatocellular, renal, breast or lung.

The polypeptide variants can be used to inhibit or reduce the proliferation of tumor cells. In such an approach, the tumor cells are exposed to a therapeutically effective amount of the polypeptide variant so as to inhibit or reduce proliferation of the tumor cell. In certain embodiments, the polypeptide variants inhibit tumor cell proliferation by at least 50%, 60%, 70%, 80%, 90%, 95% or 100%.

In certain embodiments, the polypeptide variant is used to inhibit or reduce proliferation of a tumor cell wherein the variant reduces the ability of hHGF to bind to c-Met. In other embodiments, the polypeptide variant is used to inhibit or reduce the proliferation of a tumor cell even when the polypeptide variant binds c-Met but does not substantially inhibit hHGF binding to c-Met.

In addition, the polypeptide variant can be used to inhibit, or slow down tumor growth or development in a mammal. In such a method, an effective amount of the polypeptide variant is administered to the mammal so as to inhibit or slow down tumor growth in the mammal. Accordingly, the polypeptide variants can be used to treat tumors, for example, in a mammal. The method comprises administering to the mammal a therapeutically effective amount of the polypeptide variant. The polypeptide variant can be administered alone or in combination with another pharmaceutically active molecule, so as to treat the tumor.

Generally, a therapeutically effective amount of polypeptide variant will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the polypeptide variant delivered, the formulation of the polypeptide variant, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks. A preferred route of administration is parenteral, e.g., intravenous infusion. Formulation of protein-based drugs is within ordinary skill in the art. In some embodiments of the invention, the polypeptide variant, e.g., protein-based, is lyophilized and reconstituted in buffered saline at the time of administration.

The polypeptide variants may be administered either alone or in combination with other pharmaceutically active ingredients. The other active ingredients, e.g., immunomodulators, can be administered together with the polypeptide variant, or can be administered before or after the polypeptide variant.

Formulations containing the polypeptide variants for therapeutic use, typically include the polypeptide variants combined with a pharmaceutically acceptable carrier. As used herein, "pharmaceutically acceptable carrier" means buffers, carriers, and excipients, that are, within the scope of sound medical judgment, suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers, in this regard, are intended to include any and all buffers, solvents, dispersion media, coatings, isotonic and absorption delaying agents, and the like, compatible with pharmaceutical administration. The use of such media and agents for pharmaceutically active substances is known in the art.

The formulations can be conveniently presented in a dosage unit form and can be prepared by any suitable method, including any of the methods well known in the pharmacy art. Remington's Pharmaceutical Sciences, 18th ed. (Mack Publishing Company, 1990).

In exemplary embodiments, the polypeptide variants are used for diagnostic purposes, either in vitro or in vivo, the polypeptide variants typically are labeled either directly or indirectly with a detectable moiety. The detectable moiety can be any moiety which is capable of producing, either directly or indirectly, a detectable signal. For example, the detectable moiety may be a radioisotope, such as $^{3}H$, $^{14}C$, $^{32}P$, $^{35}S$, or $^{125}I$; a fluorescent or chemiluminescent compound, such as fluorescein isothiocyanate, Cy5.5 (GE Healthcare), Alexa Fluoro® dyes (Invitrogen), IRDye® infrared dyes (LI-COR® Biosciences), rhodamine, or luciferin; an enzyme, such as alkaline phosphatase, beta-galactosidase, or horseradish peroxidase; a spin probe, such as a spin label; or a colored particle, for example, a latex or gold particle. It is understood that the polypeptide variant can be conjugated to the detectable moiety using a number of approaches known in the art, for example, as described in Hunter et al. (1962) Nature 144: 945; David et al. (1974)

Biochemistry 13: 1014; Pain et al. (1981) J. Immunol. Meth 40: 219; and Nygren (1982) J. Histochem and Cytochem. 30: 407. The labels may be detected, e.g., visually or with the aid of a spectrophotometer or other detector or other appropriate imaging system.

The polypeptide variants can be employed in a wide range of immunoassay techniques available in the art. Exemplary immunoassays include, for example, sandwich immunoassays, competitive immunoassays, immunohistochemical procedures.

In a sandwich immunoassay, two antibodies that bind an analyte or antigen of interest are used, e.g., one immobilized onto a solid support, and one free in solution and labeled with a detectable moiety. When a sample containing the antigen is introduced into this system, the antigen binds to both the immobilized antibody and the labeled antibody, to form a "sandwich" immune complex on the surface of the support. The complexed protein is detected by washing away non-bound sample components and excess labeled antibody, and measuring the amount of labeled antibody complexed to protein on the support's surface. Alternatively, the antibody free in solution can be detected by a third antibody labeled with a detectable moiety which binds the free antibody. A detailed review of immunological assay design, theory and protocols can be found in numerous texts, including Butt, ed., (1984) Practical Immunology, Marcel Dekker, New York; Harlow et al. eds. (1988) *Antibodies, A Laboratory Approach*, Cold Spring Harbor Laboratory; and Diamandis et al., eds. (1996) Immunoassay, Academic Press, Boston.

It is contemplated that the labeled polypeptide variants are useful as in vivo imaging agents, whereby the polypeptide variants can target the imaging agents to particular tissues of interest in the recipient. A remotely detectable moiety for in vivo imaging includes the radioactive atom $^{99}$mTc, a gamma emitter with a half-life of about six hours. Non-limiting examples of radionuclide diagnostic agents include, for example $^{110}$In, $^{111}$In, $^{177}$Lu, $^{18}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, or other γ-, γ-, or positron-emitters.

Non-radioactive moieties also useful in in vivo imaging include nitroxide spin labels as well as lanthanide and transition metal ions all of which induce proton relaxation in situ. In addition to imaging the complexed radioactive moieties may be used in standard radioimmunotherapy protocols to destroy the targeted cell.

A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

The disclosed polypeptide variants may also be labeled with a fluorescent marker so as to allow detection in vivo. In some embodiments, the fluorescent label is Cy5.5 (GE Healthcare). In other embodiments, the fluorescent label is an Alexa Fluoro® dye (Invitrogen). In some embodiments, the fluorescent lable is an IRDye® infrared dye (LI-COR® Biosciences).

Exemplary nucleotides for high dose radiotherapy include the radioactive atoms $^{90}$Yt, $^{131}$I and $^{111}$In. The polypeptide variant can be labeled with $^{131}$I, $^{111}$In and $^{99}$mTC using coupling techniques known in the imaging arts. Similarly, procedures for preparing and administering the imaging agent as well as capturing and processing images are well known in the imaging art and so are not discussed in detail herein. Similarly, methods for performing antibody-based immunotherapies are well known in the art. See, for example, U.S. Pat. No. 5,534,254.

EXAMPLES

The following examples are provided by way of illustration only and are not meant to limit the scope of the invention. Those of skill in the art will readily recognize a variety of non-critical parameters that could be changed or modified to yield essentially similar results.

Example 1

1.1 Protein Engineering of NK1 Through Yeast Surface Display

Figure 2:
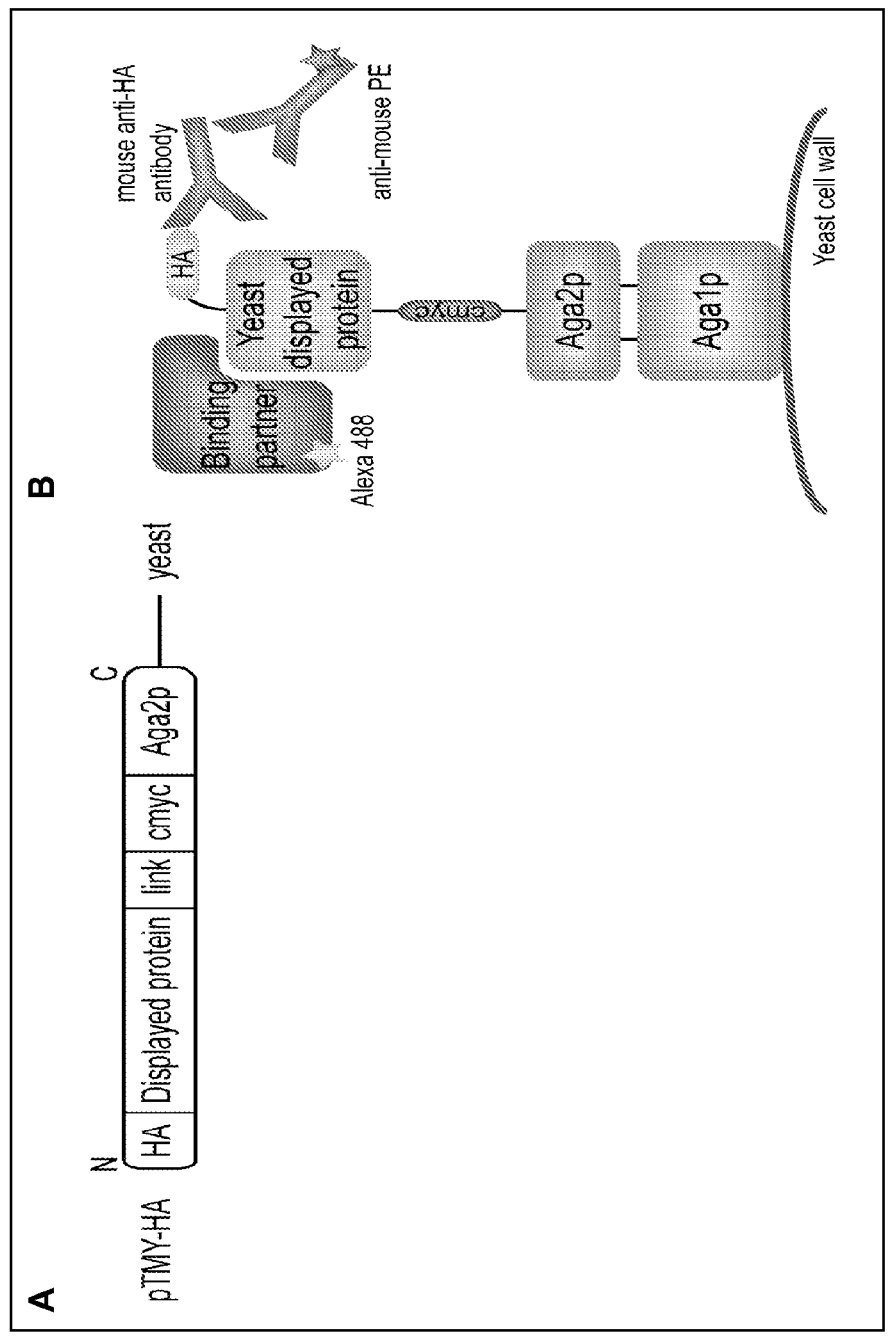
FIG. 2: Yeast display construct pTMY-HA. (A) Open reading frame of pTMY-HA. Protein is displayed with a free N-terminus and linked to Aga2p through its C-terminus. (B) Schematic of yeast surface display. The protein of interest (NK1) is tethered to yeast cell wall through genetic linkage to the N-terminus of Aga2p. Antibodies against the HA epitope tags were used to monitor cell surface expression, and interactions with a binding partner (in this case Met-Fc) were also monitored.

Yeast surface display is a powerful directed evolution technology that has been used to engineer proteins for enhanced binding affinity, proper folding, and improved stability. Combinatorial libraries of NK1 proteins were displayed on the surface of the yeast strain *Saccharomyces cerevesiae* through genetic fusion to the yeast mating agglutinin protein Aga2p. Aga2p is disulfide bonded to Aga1p, which is covalently linked to the yeast cell wall. In contrast to most yeast display studies, the construct we used here tethered the displayed NK1 proteins to the N-terminus of Aga2p (FIG. 2). It was found for this ligand-receptor system that this orientation reduced steric constraints of receptor and antibody labeling described below. The NK1 proteins were flanked by N-terminal hemagglutinin (HA) and C-terminal c-myc epitope tags, which were used to confirm expression of the construct on the yeast cell surface and to quantitate surface expression levels. A flexible $(Gly_4Ser)_3$ linker at the C-terminus of the displayed NK1 protein was used to project the protein away from the yeast cell surface to further minimize steric constraints.

Libraries of $10^7$-$10^8$ transformants were routinely created for protein engineering studies, with each yeast cell displaying thousands of identical copies of a particular NK1 mutant on its surface. High-throughput screening of tens of millions of yeast-displayed NK1 mutants using fluorescent-activated cell sorting (FACS) allowed for the isolation of protein variants with desired properties, in this case enhanced Met receptor binding affinity and/or enhanced expression. For this purpose, yeast-displayed NK1 libraries were stained with both fluorescently-labeled Met-Fc fusion protein and primary and secondary antibodies against the HA epitope tag (FIG. 2B). The use of multicolor flow cytometry enabled simultaneous and independent monitoring of both relative surface expression levels and Met binding by detecting phycoerythrin and Alexa-488 fluorescence, respectively. Yeast cells that bound the highest levels of Met and possessed the highest NK1 expression levels were isolated. Previously, a strong correlation has been shown between expression levels on the yeast cell surface, and thermal stability and soluble expression yields. The sorted yeast were propagated in culture, and the screening process was repeated several times to obtain an enriched yeast population consisting of a small number of unique clones.

Figure 3:
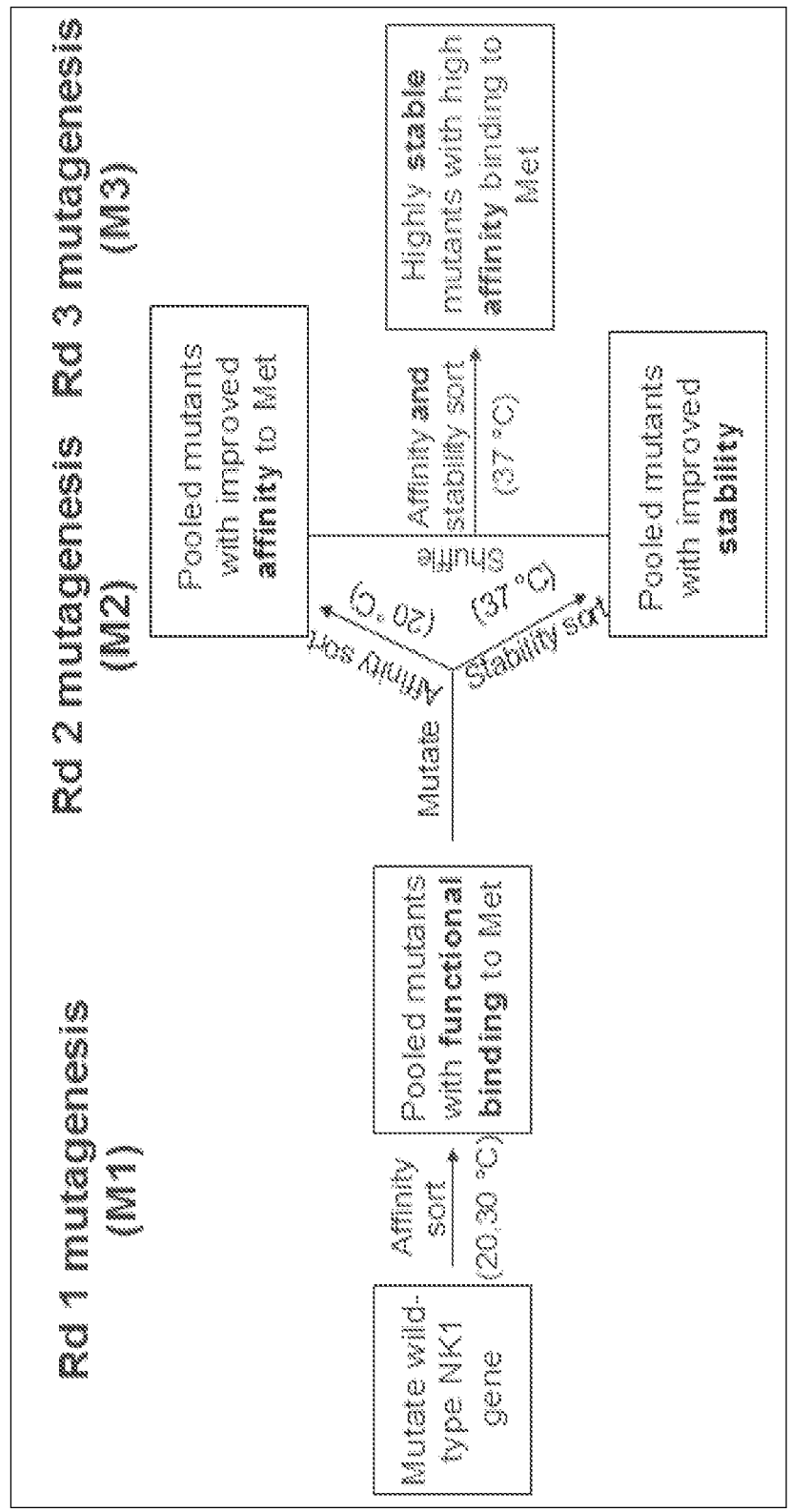
FIG. 3: Outline of NK1 engineering strategy. In first round of directed evolution (M1) library was screened for functional binding to Met; for second round (M2) library was screened in parallel for either enhanced affinity or enhance stability; for third round (M3) the M2 products were shuffled and screened simultaneously for improved affinity and stability.

1.2 Overview: Directed Evolution of NK1 for High Affinity and Stability Using Yeast Surface Display An NK1 fragment was engineered for 1) enhanced thermal stability and 2) high binding affinity to Met. A first round of directed evolution consisted largely of evolving NK1 for functional expression on the yeast cell surface and for modest improvements in Met binding affinity. Pooled products were further mutated and subjected to a second round of directed evolution in which they were screened independently for either improved Met binding affinity or enhanced stability. A third round of directed evolution was then conducted by performing DNA shuffling on pooled products from the second round, followed by screening simultaneously for improved Met binding affinity and enhanced stability (FIG. 3).

1.3 Wild-Type NK1 is not Functionally Expressed on the Yeast Cell Surface

HGF exists in two main isoforms, Isoform 1 (I1: Genbank accession no. NP_000592) and Isoform 3 (13: Genbank accession no. NP_001010932; SEQ ID NO: 63).

tively, this data demonstrates that yeast-displayed wild-type NK1 is not functionally expressed on the yeast cell surface.

1.4 Engineering NK1 for Improved Affinity and Stability Using Yeast Surface Display Three separate rounds of directed evolution were used to evolve NK1 for improvements in stability and Met binding affinity compared to wild-type NK1. Since NK1 was not functionally expressed on the yeast cell surface, the first round of directed evolution largely consisted of screening yeast-displayed NK1 mutants to isolate clones that bound to the Met receptor. Towards this goal, we generated a library of approximately $3\times10^7$ NK1 mutants by error-prone PCR using nucleotide analogs 8-oxo-dGTP and dPTP (TriLink BioTechnologies). As neither NK1 I1 nor NK1 I3 are functionally expressed on the yeast cell surface, it was not clear which isoform would be most amenable to affinity

```
(NP_00101932)
                                               SEQ ID NO: 63
MWVTKLLPALLLQHVLLHLL LLPIAIPYAE

GQRKRRNTIH EFKKSAKTTL IKIDPALKIKTKKVNTADQC ANRCTRNKGL

PFTCKAFVFDKARKQCLWFP FNSMSSGVKK EFGHEFDLYENKDYIRNCII

GKGRSYKGTVSITKSGIKCQPWSSMIPHEHSYRGKDLQENYCRNPRGEEGGPWCFTS

NPE VRYEVCDIPQ CSEVECMTCN GESYRGLMDH TESGKICQRW

DHQTPHRHKFLPERYPDKGF DDNYCRNPDG QPRPWCYTLD PHTRWEYCAI

KTCADNTMND TDVPLETTECIQGQGEGYRGTVNTIWNGIP CQRWDSQYPH

EHDMTPENFK CKDLRENYCR NPDGSESPWCFTTDPNIRVG YCSQIPNCDM

SHGQDCYRGNGKNYMGNLSQTRSGLTCSMWDKNMEDLHRHIFWEPDASKL

NENYCRNPDDDAHGPWCYTGNPLIPWDYCPISRCEGDTTPTIVNLDHPVISCAKTKQ

LRVVNGIPTRTNIGWMVSLRYRNKHICGGSLIKESWVLTARQCFPSRDLKDYEAWLG

IHDVHGRGDEKCKQVLNVSQLVYGPEGSDLVLMKLARPAVLDDFVS

TIDLPNYGCTIPEKTSCSVY GWGYTGLINY DGLLRVAHLY IMGNEKCSQH

HRGKVTLNES EICAGAEKIG SGPCEGDYGG PLVCEQHKMR MVLGVIVPGR

GCAIPNRPGI FVRVAYYAKW IHKIILTYKV PQS
```

Figure 4:
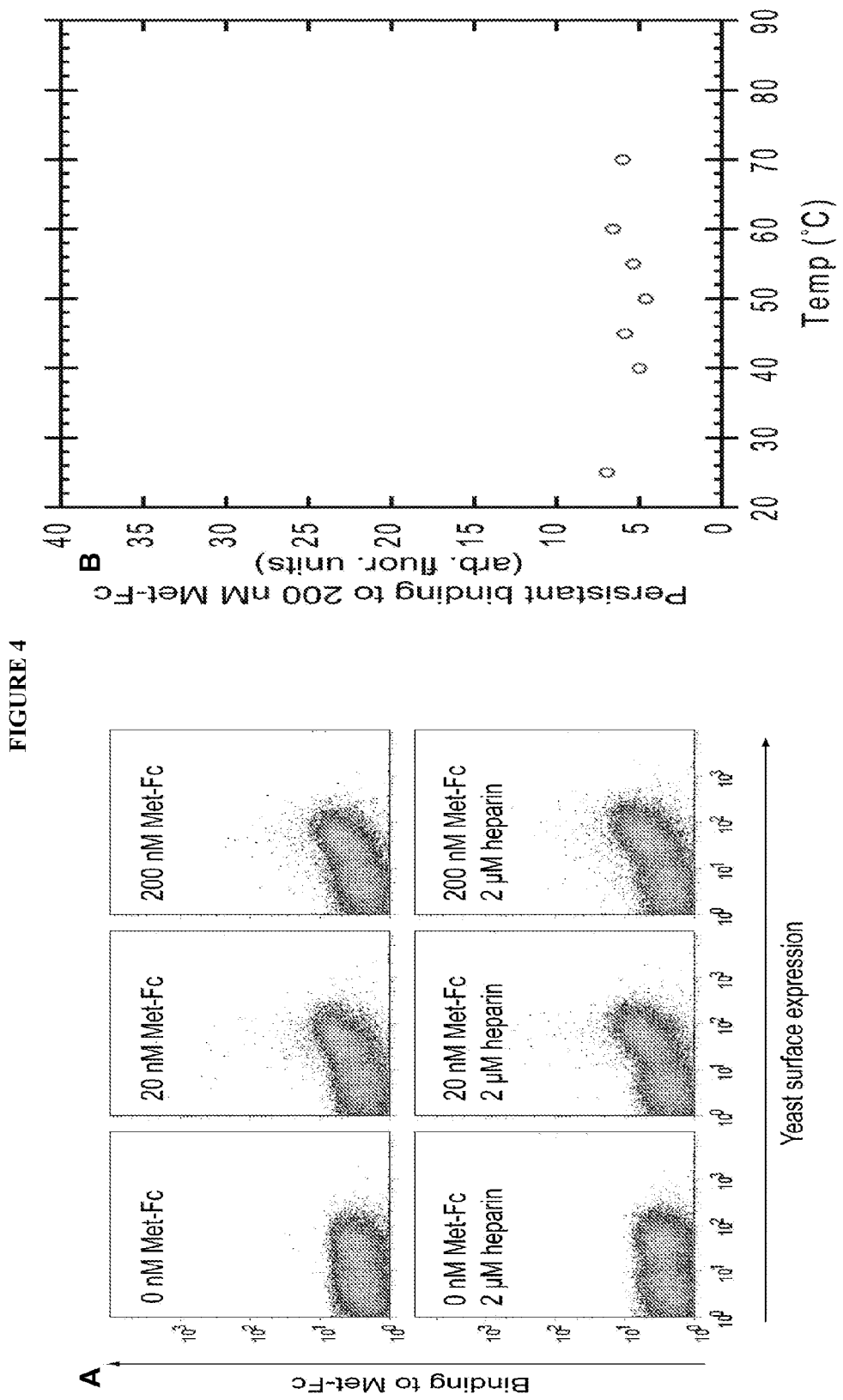
FIG. 4: Yeast-displayed wild-type NK1 does not bind to Met. (A) Relative binding by yeast-displayed NK1 I1 to soluble Met-Fc A488 in the absence (top) or presence (bottom) of 2 μM heparin. Levels of binding is unchanged for 20 or 200 nM Met-Fc. (B) Relative binding of yeast-displayed NK1 I1 following heating to various temperatures. Background binding levels observed in (A) are unchanged even following heating to 70° C.

HGF I1 and I3 are identical in sequence, except for a 5 amino acid deletion in the first Kringle domain (K1) of I3. Yeast display plasmid, pTMY-HA, was used to express NK1 I1 or NK1 I3 on the yeast cell surface as a genetic fusion to the yeast cell wall protein Aga2p (FIG. 2). Similar results were found for both NK1 I1 and NK1 I3. Yeast-displayed NK1 I1 was stained for relative expression (through antibody detection of the HA tag) and binding to 20 or 200 nM of Met-Fc (R&D Systems) labeled with Alexa 488. Since heparin is required for the wild-type NK1-Met interaction, this experiment was conducted both in the presence (FIG. 4A, top) and absence (FIG. 4A, bottom) of 2 µM heparin (Lovenox, Sanofi-Aventis). Flow cytometry was used to detect yeast expressing NK 1 µl on the yeast cell surface. Only low levels of binding to soluble Met-Fc was observed (FIG. 4, x-axis vs. y-axis). Binding levels are shown after heating yeast-displayed NK1 to 70° C. (FIG. 4B). As shown below, soluble NK1 I1 produced from the yeast *Pichia pastoris* is completely unfolded at 60° C. (FIG. 4). Collecmaturation through directed evolution. Therefore, we used equal amounts of NK1 I1 and NK1 I3 as starting templates to generate a combined NK1 mutant library based on both I1 and I3. Sequencing of random clones from the yeast-displayed library confirmed equal representation of NK1 I1 and NK1 I3.

Figure 5:
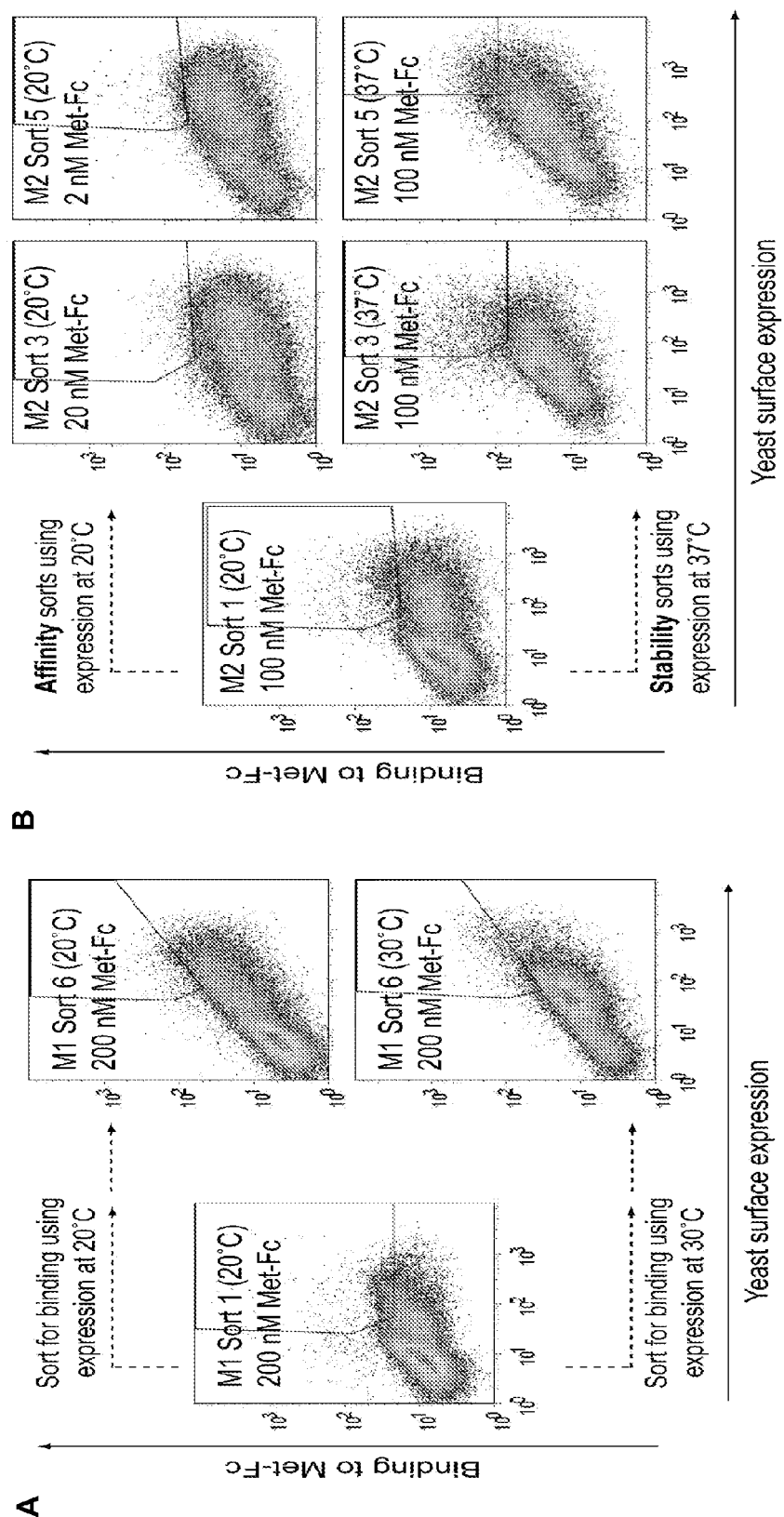
FIG. 5: Sort progression for round 1 (M1) and round 2 (M2) of directed evolution. (A) Sort progression for M1. Mutants were sorted by flow cytometry using either 20° C. or 30° C. expression temperature. Following six rounds of sorting, the bulk library population exhibited detectable binding to Met-Fc A488. (B) Sort progression for M2, denoting Affinity and Stability sort performed in parallel. Affinity sorts were screened for improved binding to decreasing concentrations of Met-Fc A488, while Stability sorts were screened for binding to 100 nM Met-Fc A488 and improved expression at 37° C. Temperatures in parenthesis denote the yeast surface expression temperature used for the particular sort.

Yeast prefer to grow at 30° C., however, they often show improved expression of more complex proteins at 20° C. Therefore, two rounds of library sorting were conducted after inducing protein expression on the yeast cell surface at 20° C. to enable improved folding of NK1 mutants, and FACS was used to isolated yeast cells that exhibited detectable binding to 200 nM Alexa-488 labeled Met-Fc (Met-Fc A488) (FIG. 5A). Subsequent library sorts were conducted in parallel using either 20° C. or 30° C. induction temperatures with the goal of screening for mutants with improved stability using the 30° C. expression temperature. After five rounds of sorting with each strategy (5 rounds using 20° C. expression temperature, or 2 rounds with 20° C. followed by 3 rounds with 30° C. expression temperature) the library clearly contained members that bound to 200 nM Met-Fc.

For a second round of directed evolution pooled mutants from the final sorts of the first round of directed evolution were randomly mutated by error-prone PCR to generate a library of approximately 8×10⁷ unique mutants. The first two rounds of sorting of this library were conducted using a 20° C. expression temperature to first recover mutants that bound to soluble Met-Fc A488. For subsequent rounds, we sorted in parallel either for improvements in expression (i.e. folding stability), which has been shown to correlate to improved thermal stability, or for improvements in Met binding affinity (FIG. 5B). Expression at elevated temperatures (37° C.) was used to impart sorting stringency for improved stability, while improved binding to decreasing concentrations of soluble Met-Fc A488 was used for affinity sorting stringency.

Figure 6:
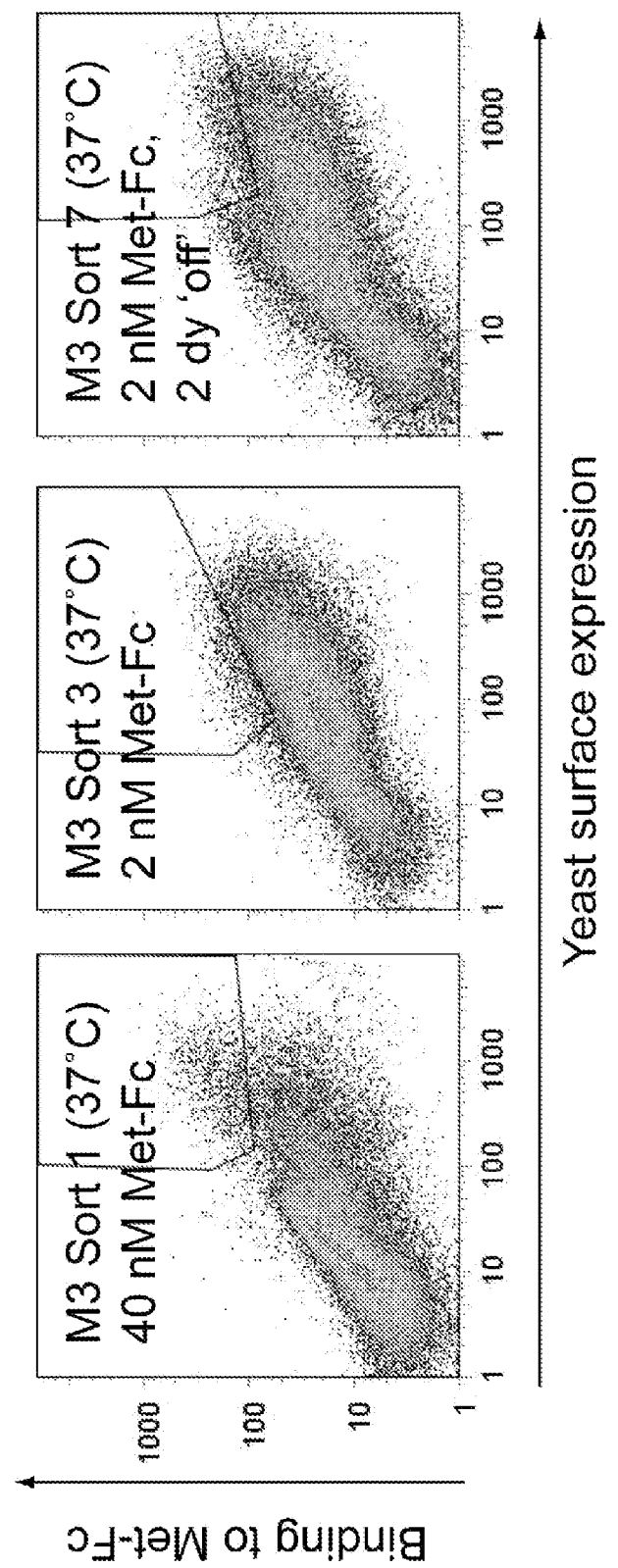
FIG. 6: Sort progression for round 3 (M3) of directed evolution. Library was sorted in parallel for improved affinity and stability by screening for improved binding to decreasing concentrations of Met-Fc A488 using 37° C. expression temperature. Sort 7 was conducted by staining with 2 nM Met-Fc A488 following by a two day unbinding step (off) in the presence of excess competitor.

Finally, a third round of directed evolution consisted of DNA shuffling of the final pools of the stability- and affinity-enhanced mutants from the second round of directed evolution to generate a third generation library of approximately 2×10⁷ unique transformants. This library was simultaneously screened for both enhanced stability (via high cell surface expression level upon 37° C. induction) and enhanced affinity (through improved binding to substantially decreasing concentrations of Met-Fc A488). The first, second and third rounds of sorting used 40, 20 and 2 nM Met-Fc A488, respectively. After three rounds of sorting, the resulting pool of mutants expressed well at 37° C. and bound strongly to 2 nM Met-Fc A488 (FIG. 6, middle). Subsequent sorts were conducted by labeling with 2 nM Met-Fc A488, followed by an unbinding step in the presence of excess unlabeled competitor, in this case recombinant HGF (R&D Systems). Clones that retained Met binding after 24 hr in the presence of excess HGF competitor were isolated by FACS. This process was repeated until a pool of NK1 mutants that retained binding to Met-Fc A488 following a 2 day unbinding step in the presence of excess HGF as a Met-Fc competitor (FIG. 6, right).

A pool of NK1 variants was identified in which the variants are efficiently expressed on the yeast cell surface at elevated temperatures and maintain persistent binding to 2 nM soluble Met even after a 2 day unbinding step in the presence of excess HGF competitor (FIG. 6).

1.5 Sequence Analysis of Affinity and Stability-Enhanced NK1 Mutants

In parallel to performing Round 3 of directed evolution, characterization began of promising mutants from Round 2. Eight random mutants were sequenced from each of the final two sort rounds for each sorting strategy (20° C. affinity sort strategy, and 37° C. stability sort strategy). Interestingly, all 32 clones sequenced were based on NK1 I1, even though sequencing of the initial library indicated relatively equal proportions of NK1 Isoform 1 and Isoform 3. Additionally, a number of favored or consensus mutations were evident. 10 mutations repeatedly appeared in clones randomly sequenced from the library sort products, and eight of these mutations were present in over half of the randomly selected clones. These dominant mutations are highlighted in bold in Table 1. Due to the wide variety of mutations, none of the individual clones contained all eight of these mutations. However, one clone contained five of the eight most frequent mutations (K62E, N127D, K137R, K170E, N193D; this clone is termed M2.1). The remaining three mutations (Q95R, K132N, Q173R) were added onto the background of this clone to generate the NK1 mutant we termed M2.2.

Further sequence analysis of these mutations highlighted a number of interesting observations, which are further discussed below.

The sort products from the two strategies did not produce many of the exact same clones, but did however exhibit a remarkable overlap in consensus sequences. The negative correlation between I125T and N127D observed in the M2 (second round directed evolution) products persisted with the M3 (third round directed evolution) products. Of the 30 sequenced clones, 25 contained the N127D mutation, none of which also contained the I125T mutation. However, each of the five clones not containing N127D did contain the I125T mutation. K62E/V64A and I130V/K132N consensus mutations occurred with only a 2 amino acid spacing.

All of the eight consensus mutations from M2 products were present in the M3 products (recall M2.2=K62E, Q95R, N127D, K132N, K137R, K170E, Q173R, N193D). There were five additional consensus mutations that arose in over 50% of the M3 products: V64A, N77S, I130V, S154A, and F190Y.

TABLE 4

Sequence Sustitutions Present in Certain Variants

| Protein | | Mutations | Activity |
|---------|---|-----------|----------|
| NK1 | | None (wild-type NK1) | Agonist |
| M2.2 | | K62E, Q95R, N127D, K132N, K137R, K170E, Q173R, N193D | Weak agonist |
| M2.2 D127N | | K62E, Q95R, K132N, K137R, K170E, Q173R, N193D (an N127D mutation in M2.2 was reverted back to the wild-type 'N'. | Agonist |
| M2.2 D127A | | K62E, Q95R, N127A, K132N, K137R, K170E, Q173R, N193D | Antagonist |
| M2.2 D127K | | K62E, Q95R, N127K, K132N, K137R, K170E, Q173R, N193D | Antagonist |
| M2.2 D127R | | K62E, Q95R, N127R, K132N, K137R, K170E, Q173R, N193D | Antagonist |
| Aras-4 | M3S7.2.11 | R33G, K58R, K62E, V64A, N77S, Q95R, D123A, N127D, K132R, S135N, K137R, S154A, K170E, Q173R, F190Y, N193D | Antagonist |

Example 2

Figure 7:
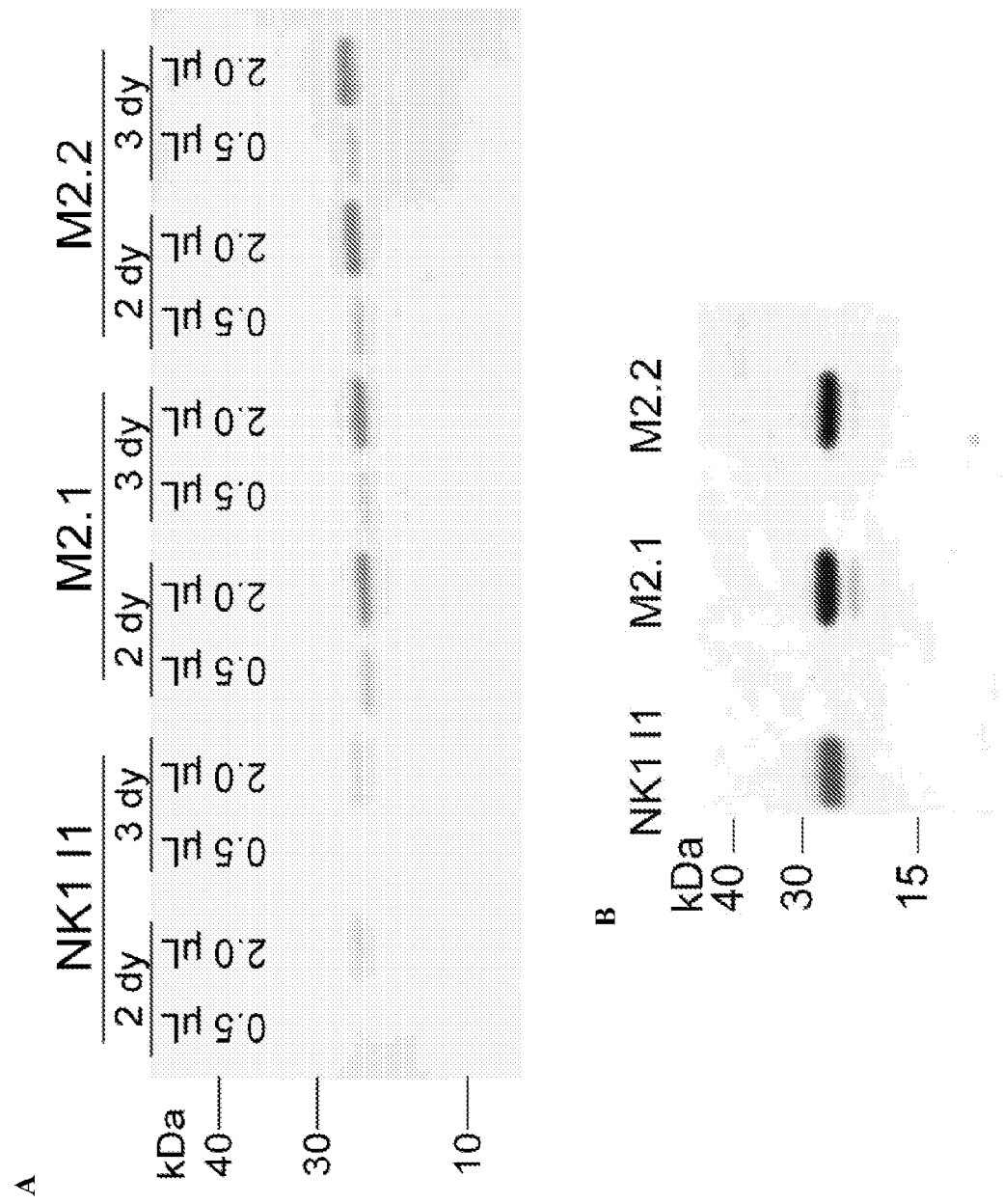
FIG. 7: Recombinant expression of wild-type NK1 I1, M2.1, and M2.2 in *P. pastoris*. (A) Western blot of supernatants following expression at 30° C. (B) Coomassie stained gel of purified NK1 I1, M2.1, and M2.2.

2.1 Soluble Production of Wild-Type NK1 and NK1 Mutants in the Yeast Strain P. Pastoris Briefly, DNA encoding for wild-type NK1, M2.1, or M2.2 containing an N-terminal FLAG epitope tag (DYKDDDDK) and a C-terminal hexahistidine tag were cloned into the secretion plasmid pPIC9K. Constructs were transformed into P. pastoris, and were selected for growth on YPD-agar plates containing 4 mg/mL Geneticin and screened for NK1 expression by Western blotting of culture supernatant. FIG. 7A shows that M2.1 and M2.2 express well at 30° C., while wild-type NK1 expresses at much lower levels. This data is in agreement with previous studies that report engineering for enhanced protein stability using yeast-surface display also confers improved recombinant expression levels. However, reducing the expression temperature to 20° C. enabled efficient expression of wild-type NK1 (data not shown). NK1 and mutant expression were scaled up to 0.5 L in shake flask cultures and purified using immobilized nickel affinity chromatography followed by gel filtration on a Superdex™ 75 column (GE Healthcare). Several milligrams of mutants M2.1 and M2.2 were obtained from one 0.5 L shake flask, without any optimization, indicating that even higher yields could be obtained by modifying induction conditions or through fermentation.

2.2 Mutants M2.1 and M2.2 Exhibit Higher Thermal Stability than Wild-Type NK1

Figure 8:
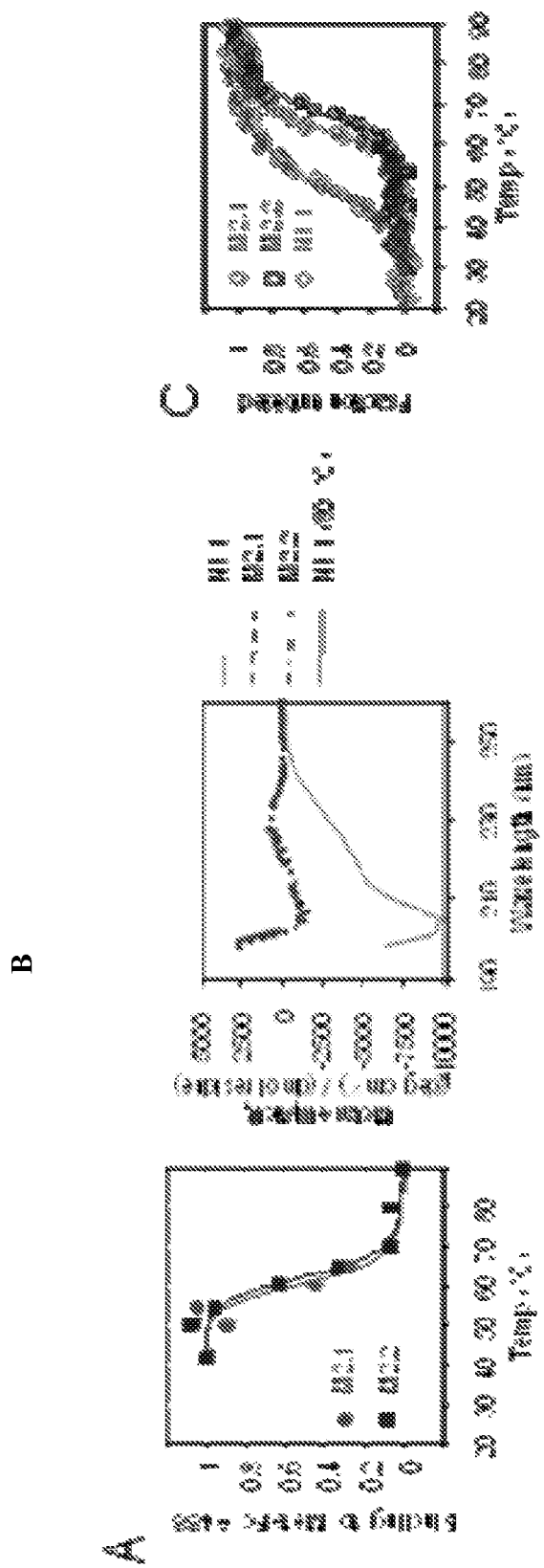
FIG. 8: Thermal stability of NK1 mutants. (A) Yeast surface-displayed M2.1 and M2.2. Wild-type NK1 was not functionally expressed on the yeast surface, so stability could not be assessed in this manner. (B) Thermal stability of soluble NK1 proteins as determined by variable temperature CD scans. (C) The unfolding of this secondary structure was monitored by variable temperature CD scans.

To test thermal stability, M2.1 and M2.2 were expressed on the yeast cell surface, heated to varying temperatures, and the retention of binding to fluorescently labeled Met-Fc was measured by flow cytometry (FIG. 8A). NK1 mutants M2.1 and M2.2 have $T_m$ values on the surface of yeast of 61.0±1.4° C. and 61.4±0.7° C., respectively. It was not possible to monitor stability of yeast-displayed wild-type NK1 since it was not functionally expressed on the yeast cell surface.

To test the stability of soluble proteins, secondary structure unfolding of purified, soluble mutants was monitored using circular dichroism (CD) on a Jasco J-815 CD spectrometer. CD scans of the mutant proteins identified a peak at 208 nm, owing largely to the β-sheet structural element. The CD scans of M2.1 and M2.2 resembled that of wild-type NK1, illustrating the mutant proteins contain the same overall secondary structural elements as wild-type NK1 (FIG. 8B). A CD spectra of wild-type NK1 at 80° C. resembles that of a random coil, demonstrating the ability to monitor the unfolding of secondary structural elements using circular dichroism (FIG. 8B) Using this information, the unfolding of this secondary structure was monitored by variable temperature CD scans (FIG. 8C). In each of these assays, the M2.1 and M2.2 exhibited higher thermal stability (63.6±0.3° C. and 67.8±0.2° C., respectively) compared to wild-type NK1 ($T_m$=50.9±0.2° C.). To further confirm these results, the melting of a local maxima at 236 nm to that of a random coil for M2.1 was monitored. The same $T_m$ was observed for melting at 208 nm. A summary of thermal stability ($T_m$) of wild-type and mutant NK1 proteins as determined by CD temperature melts is shown in Table 5.

TABLE 5

| | Tm ± std. dev. (° C.) |
|---|---|
| NK1 | 50.7 ± 0.2 |
| NK1 N127A | 47.9 ± 0.7 |
| M2.1 | 63.9 ± 0.5 |
| M2.2 | 69.0 ± 1 |
| M2.2 D127N | 65.5 ± 0.5 |
| M2.2 D127A | 63.7 ± 0.1 |
| M2.2 D127K | 62.5 ± 0.1 |
| M2.2 D127R | 62.3 ± 0.5 |

2.3 The Effects of Salt Concentration on Protein Stability

Figure 9:
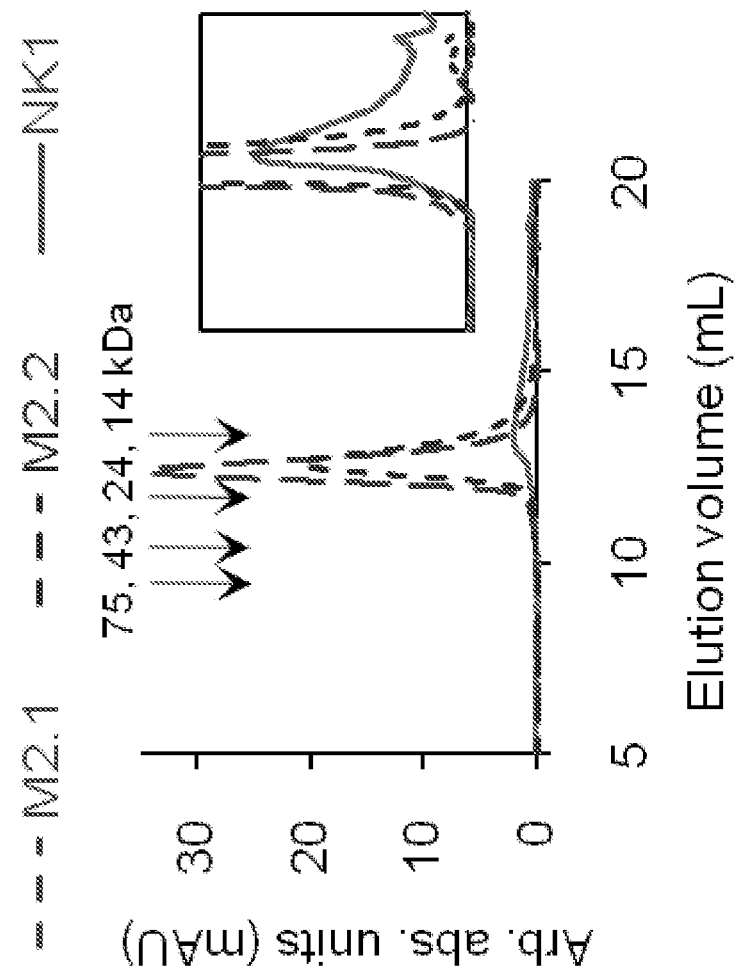
FIG. 9: Stability of wild-type and mutant NK1 proteins. NK1 proteins analyzed by size exclusion chromatography under reduced salt concentrations (137 mM NaCl). Inset, close-up trace of wild-type NK1.

To retain its structural integrity, it was observed that wild-type NK1 must be maintained in buffer containing high salt concentrations (>200-300 mM NaCl). As further evidence of this requirement, wild-type NK1 exhibited a broad, delayed elution profile on size exclusion chromatography with buffer containing moderate salt concentration (137 mM) (FIG. 9 and inset), suggesting unfolding and/or non-specific binding to the column under these conditions. In contrast, M2.1 and M2.2 eluted as a single, sharp peak on size exclusion chromatography under similar moderate salt conditions (FIG. 9).

Example 3

3.1 Point Mutations at the NK1 Homodimerization Interface

Residue N127 lies within the linker region connecting the N and K1 domains (FIG. 1). The side chain of this asparagine residue forms two hydrogen bonds. The N127D variant was frequently observed among the library-isolated variants. (Tables 2 and 3). To probe the effects of the N127D mutation within M2.2 on biological activity, a series of point mutants were generated at this position. An alanine residue transforms wild-type NK1 from an agonist into an antagonist by disrupting stabilizing interactions of the NK1 homodimer. The effects of mutations to lysine or arginine at this position were tested. These substitutions introduce steric and electrostatic obstructions through bulky, charged side-chains.

In addition, the point mutant D127N was analyzed; this reverts this position back to the wild-type asparagine residue. Within the context of M2.2, which contains the N127D mutation, these mutations are referred to as D127A, D127K, D127R, and D127N. Importantly, each of these mutants retained the high thermal stability associated with M2.2 (Table 5).

3.2 Characterization of NK1 Mutants as Met Receptor Agonists or Antagonists

The NK 1 mutants were evaluated in MDCK cell scatter and uPA assays, two assays widely used to study activation of the Met receptor in mammalian cells. For MDCK cell scatter assays, 1500 cells/well were seeded into 96-well plates in 100 μL of complete growth media and incubated at 37° C., 5% $CO_2$. After 24 h, media was removed by aspiration and replaced with media containing HGF or NK1 proteins at a concentration of 0.1 or 100 nM, respectively. In some experiments Lovenox® heparin (Sanofi-Aventis) was used at a concentration of 2 μM or at a 2:1 molar ratio of heparin:NK1. After 24 h, cells were fixed and stained with 0.5% crystal violet in 50% ethanol for 10 min at room temperature, washed with water, and dried in air prior to being photographed. MDCK scatter inhibition assays were performed is a similar manner, except cells were incubated with 250 nM NK1 mutants for 30 min prior to adding HGF at a final concentration of 0.1 nM.

For MDCK uPA assays, 4000 cells/well were seeded into 96-well plates in 100 μL of complete growth media and incubated at 37° C., 5% $CO_2$. After 24 h, media was removed by aspiration and replaced with media containing HGF or NK1 at a concentration of 1 or 100 nM, respectively. After 24 h, cells were washed two times with 200 μL phenol red-free DMEM and incubated with 200 μL reaction buffer containing 50% (vol/vol) of 0.05 units/mL plasminogen (Roche Applied Science), 40% (vol/vol) 50 mM Tris pH 8.0, 10% (vol/vol) and 3 mM chromozym PL (Roche Applied Science) in 100 mM glycine pH 3.5 solution. Plates were incubated for 4 h at 37° C., 5% $CO_2$ prior to measuring absorbance at 405 nm using an Infinite M1000 microplate reader (Tecan Group Ltd.).

Figure 10:
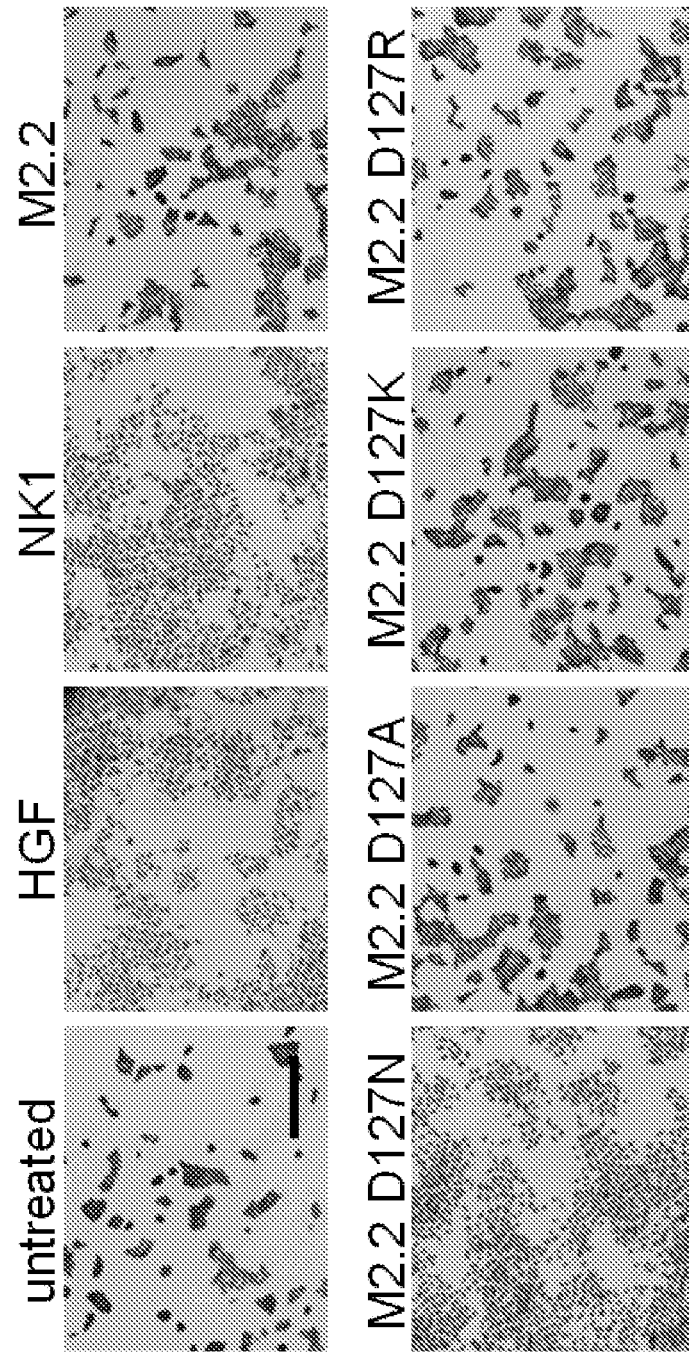
FIG. 10: Cellular activity of wild-type and mutant NK1 proteins. Agonistic activity of HGF (0.1 nM) or NK1 proteins (100 nM) was measured in a MDCK scatter assay in the presence of 2 μM heparin. Scale bar=500 μm.

The mutants M2.2 D127A, D127K, and D127R did not induce Met activation, as measured by scatter (FIG. 10 and FIG. 11A) or uPA activation (FIG. 11B) in MDCK cells. The unmodified M2.2 variant, which contains the N127D mutation, exhibited weak (FIG. 11A) or no agonistic activity (FIG. 10 and FIG. 11B).

Figure 11:
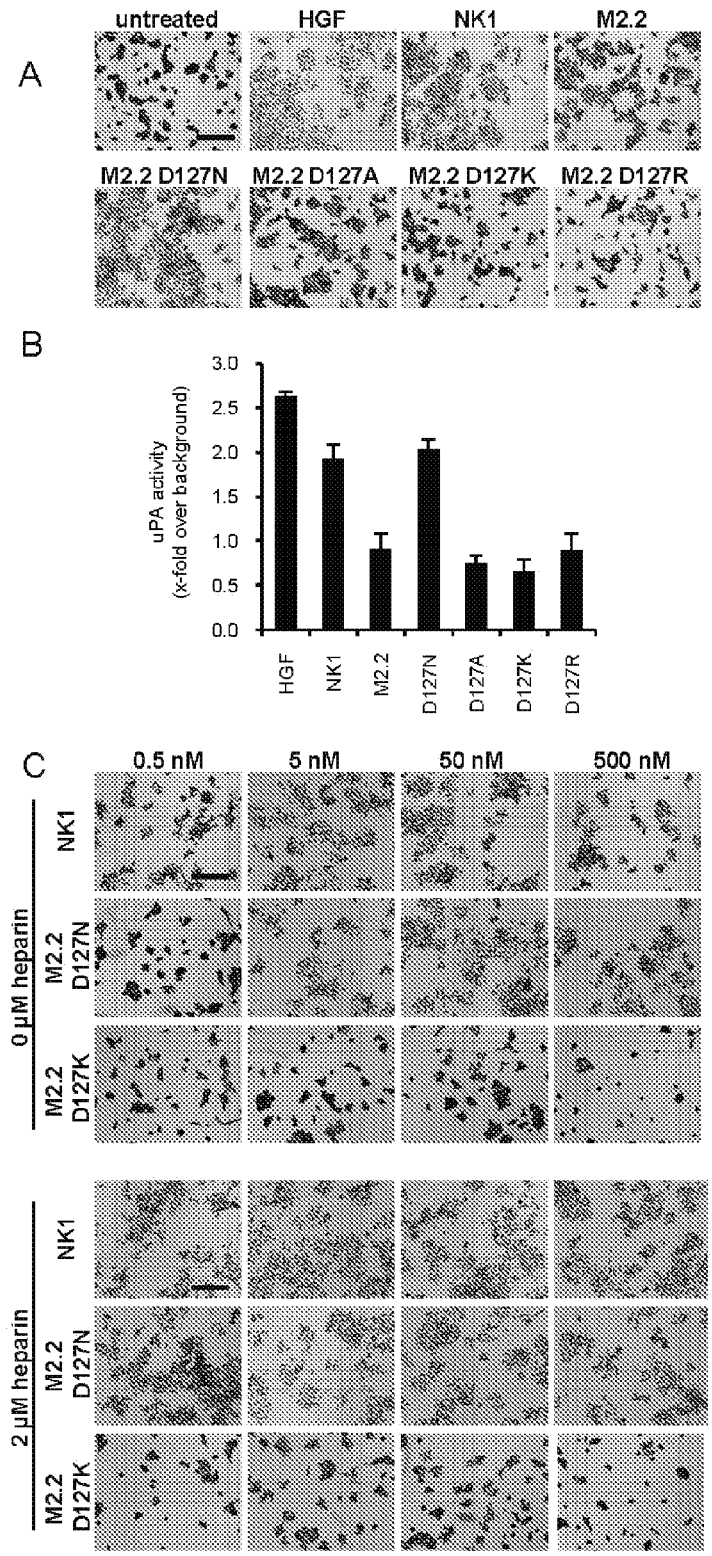
FIG. 11: Agonistic activity of wild-type and mutant NK1 proteins. (A) MDCK scatter assay by HGF (0.1 nM) or NK1 proteins (100 nM) in the absence of heparin. (B) Urokinase-type plasminogen activator (uPA) induced by HGF (1 nM) or NK1 proteins (100 nM) in the absence of heparin. (C) MDCK scatter assay, testing a range of concentrations of wild-type NK1, M2.2 D127N, or M2.2 D127K in the absence (top) or presence (bottom) of 2 μM heparin. Images are representative of experiments performed on separate days. Scale bar: 500 μm.

In contrast, reversion of position 127 to the wild-type asparagine residue (M2.2 D127N) resulted in agonistic activity in both MDCK scatter (FIG. 10 and FIG. 11A) and uPA assays (FIG. 11B). The activity of M2.2 D127N was similar to that of wild-type NK1, and both showed enhanced activity in the presence of soluble heparing (FIG. 11C top vs. bottom). In comparison, M2.2D127A, D127K, and D127R did not exhibit agonistic activity in these assays either in the presence of absence of heparin (FIG. 10 and FIG. 11A-C).

Figure 12:
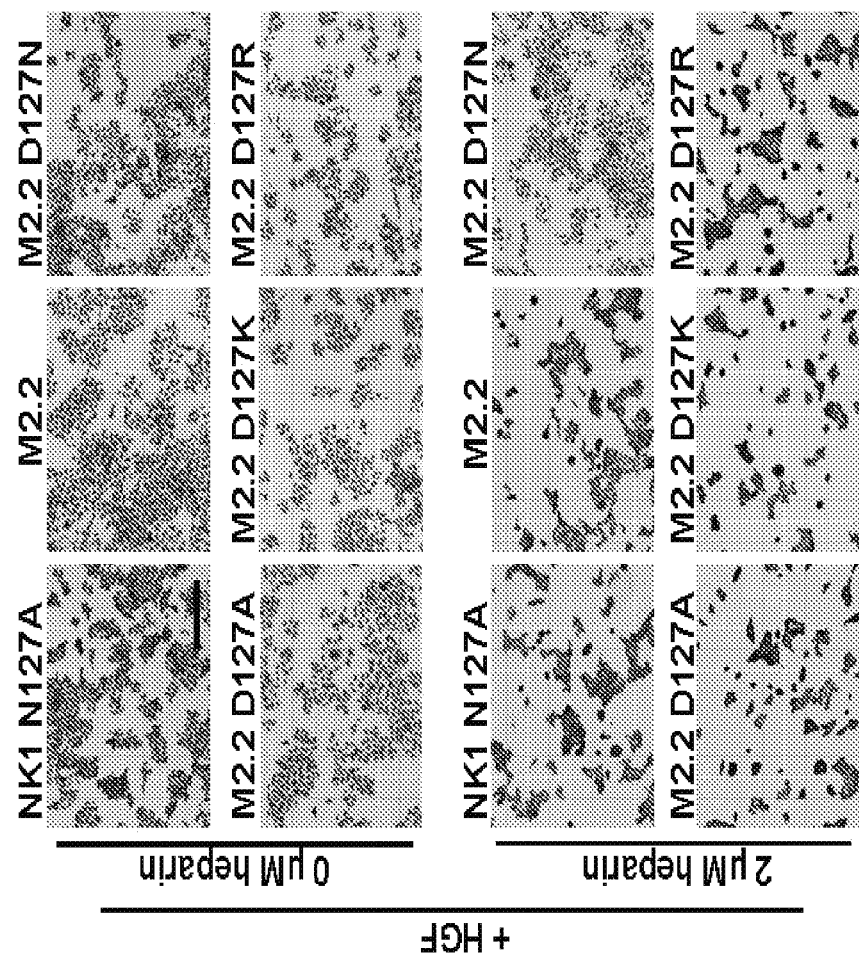
FIG. 12: Antagonistic activity of wild-type and mutant NK1 proteins. Inhibition of HGF-induced MDCK scatter (0.1 nM HGF) by NK1 mutants (250 nM) in the absence (top) or presence (bottom) of 2 μM heparin. NK1 N127A is a previously reported antagonist based on wild-type NK1. Images are representative of experiments performed on separate days. Scale bar: 500 μM.

The ability of these mutants to inhibit HGF-induced Met activation was tested. As a control, M2.2 D127N did not inhibit HGF-induced activity, providing further evidence of its functions as a Met receptor agonsit (FIG. 12). M2.2 mutants D127A, D127K, and D127R exhibited weak or minimal inhibition of HGF-induced MDCK scattering in the absence of soluble heparin (FIG. 12 top)

Figure 13:
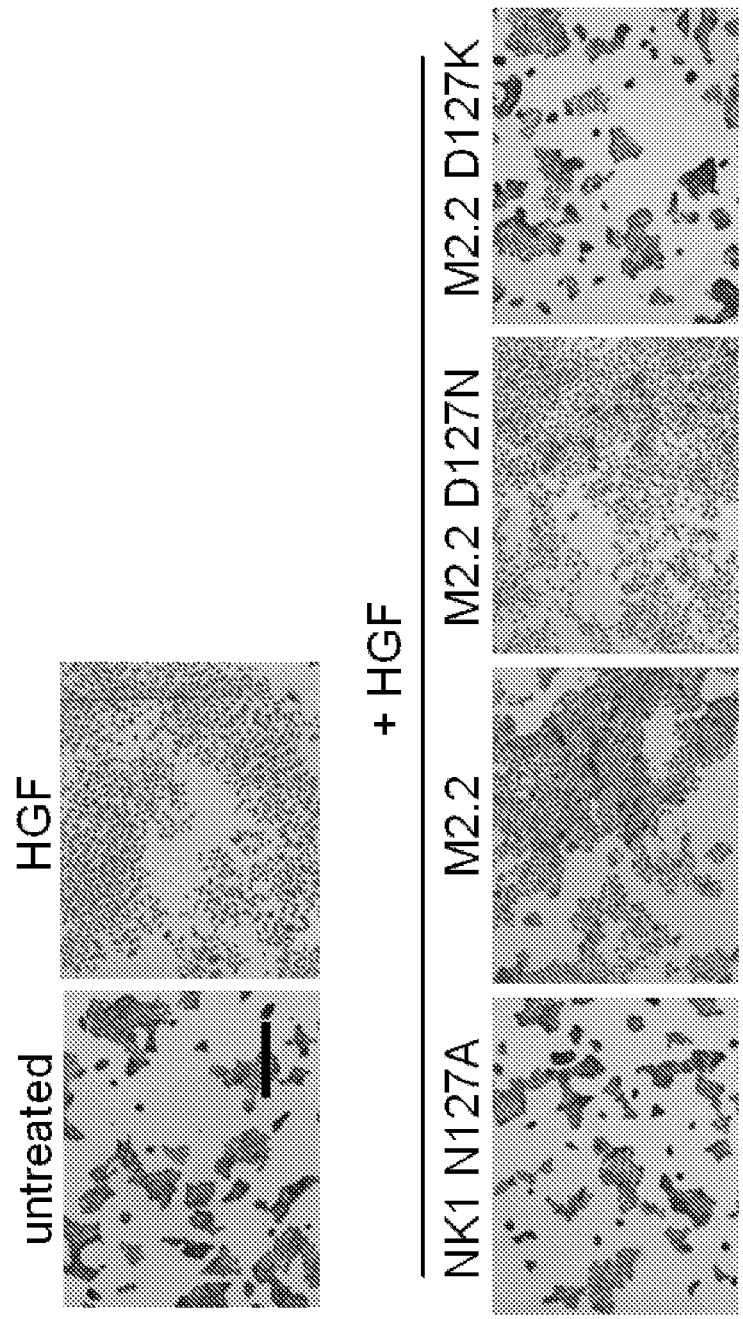
FIG. 13: Cellular activity of wild-type and mutant NK1 proteins. Inhibition of HGF-induced activity (0.1 nM) was measured in a MDCK scatter assay with NK1 proteins (250 nM) formulated with a 2:1 molar ratio of heparin. Untreated MDCK cells were used as a negative control. Images are representative of experiments performed on separate days. Scale bar=500 μm.

In contrast, strong antagonistic activity was observed with the addition of 2 µM heparin (FIG. 12 bottom). Pre-formulating the NK1 mutants with a 2:1 molar ratio of heparin:NK1 was sufficient to confer this antagonistic activity and obviated the need to add excess heparin for improved antagonistic activity (FIG. 13). Unmodified M2.2 (M2.2 N127D) exhibited only weak antagonistic activity with a 2:1 molar ratio of heparin (FIG. 13), supporting the utility of the rationally-engineered point mutations. The antagonistic activity of M2.2 D127K is similar to that of previously reported antagonist NK1 N127A (FIG. 13). However, the M2.2 D127A/K/and R mutants possess markedly improved stability and expression compared to NK1 N127A, namely lower salt-dependent stability, an increased $T_m$ of ~15° C. and ~40-fold improved recombinant expression yield, which are all attractive properties.

4.1 Biochemical and Biological Characterization of Recombinant Aras-4

Figure 14B:
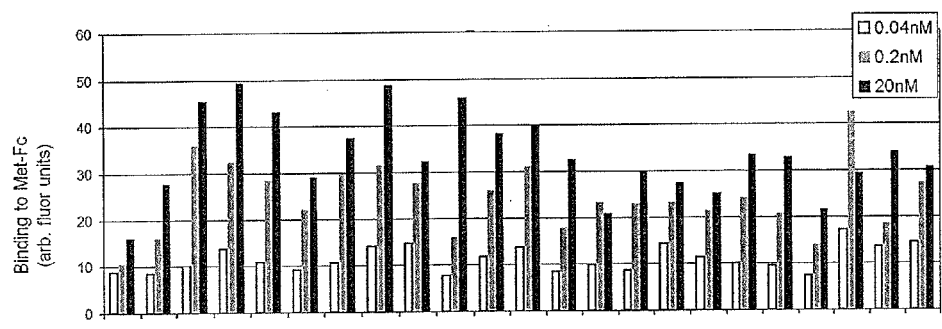
FIG. 14: Expression of NK1 mutants on the yeast surface and binding to fluorescent Met-Fc as measured by flow cytometry. (A) Binding of soluble Met-Fc conjugated to Alexa-488 (Met-Fc A488) to yeast-displayed NK1 mutants from the second (M2.1, M2.2) and third (M3S7.X.XX) rounds of directed evolution. [Met-Fc A488]: 20 nM (black), 0.2 nM (grey) and 0.04 (white). M2.1 is a clone from round 2 that contained five of the eight most commonly occurring mutations, and M2.2 was generated by site-directed mutagenesis comprising all eight of the most common mutations from the second round of directed evolution. Each of the mutants from the third round of directed evolution binds more strongly than M2.1, and many show improvement over M2.2. (B) Expression of NK1 mutants on the yeast cell surface as measured by fluorescent antibodies against a terminal epitope tag. Five NK1 mutants that had high expression levels, Met-Fc binding were chosen for soluble production and further characterization (boxed).
Figure 14A:
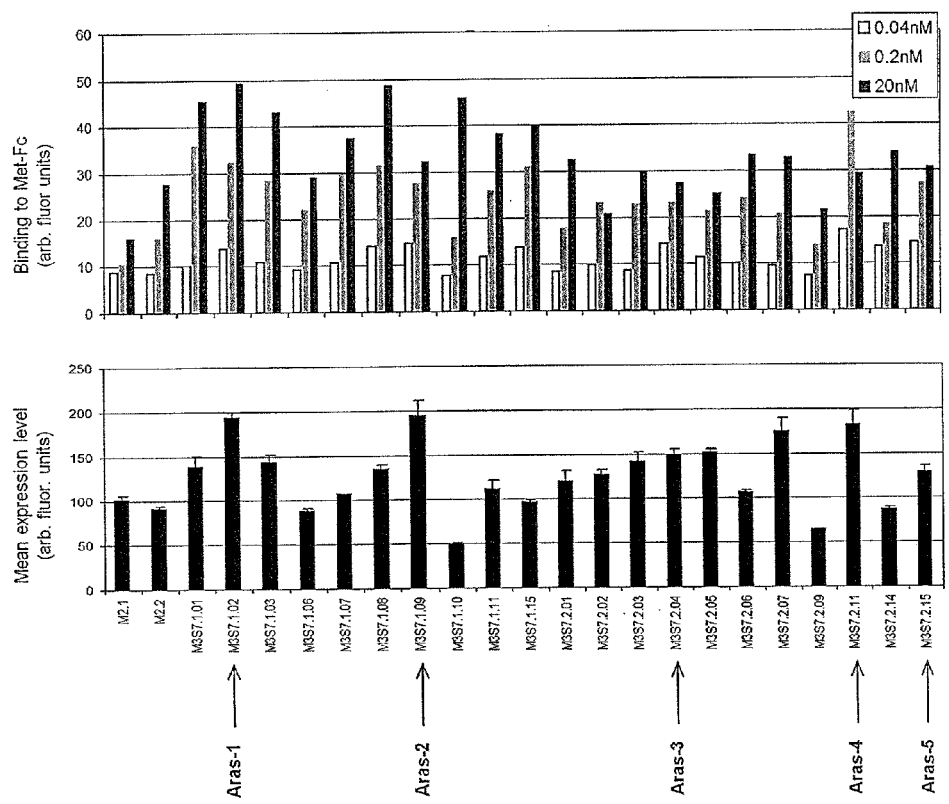

Five of the clones from the third round of directed evolution were selected for further investigation, based on their sequence distribution, yeast surface expression level, and Met-Fc binding. These clones were referred to as Aras-1, -2, -3, -4, and -5 (FIG. 14). Each of these clones was found to be well expressed in the yeast *Pichia pastoris* except for Aras-1.

Figure 15:
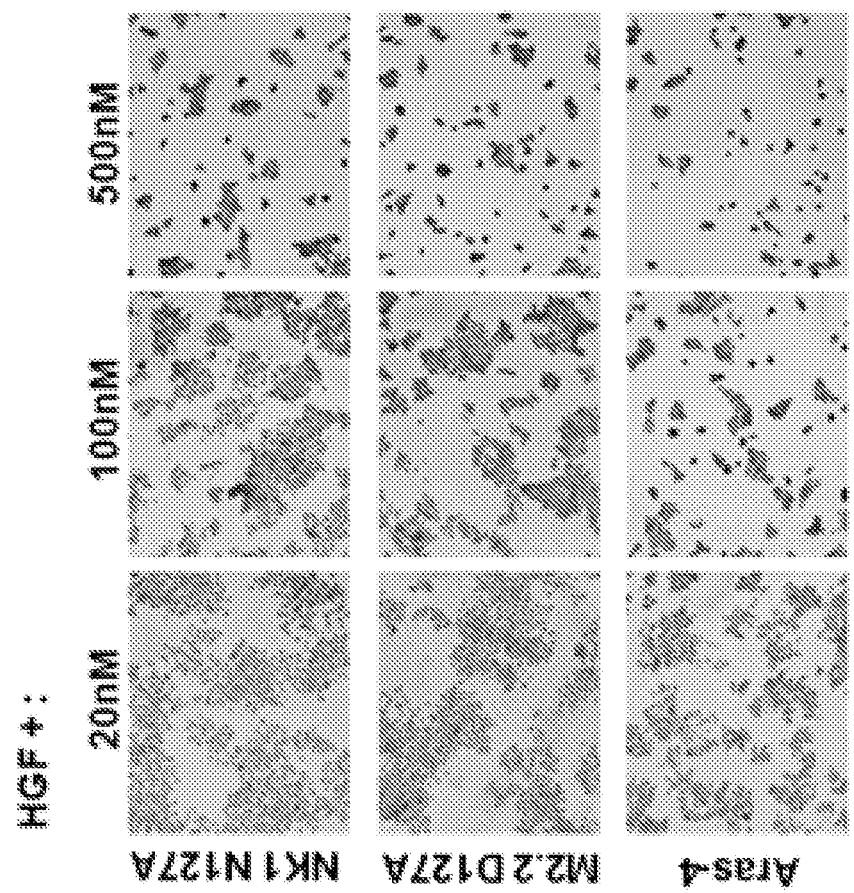
FIG. 15: Aras-4 Potently Inhibits HGF-induced Met Activity. The effect of Aras-4, M.2.2D127A, and NK1 N127A on Met activation was assayed using Madine-Darby canine kidney (MDCK) cells in the presence of various concentrations of HGF (20, 100, or 500 NM).

Aras-4 was selected for further characterization. It exhibited high thermal stability as determined by CD temperature melts ($T_m$=64.9±1.2° C.). Aras-4 does not activate cellular Met when added to a culture of MDCK cells and effectively inhibited HGF-induced activation of Met at approximately a five-fold lower concentration than M2.2 D127A or the wild-type NK1-based antagonist NK1 N127A (FIG. 15).

4.2 Introduction of Disulfide Linkages to Form Covalently Bound Dimers

Figure 16A:
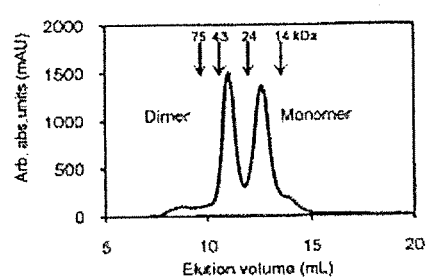
FIG. 16: Introduction of Cysteine at the N-Terminus of Variant Proteins Results in Partial Monomer/Dimer Formation. A) FPLC trace of Ni-NTA-purified cystine dimer M2.2 D127N (cdD127N), showing a mixture of dimeric and monomeric forms. Absorbance was monitored at 280 nm.
Figure 16B:
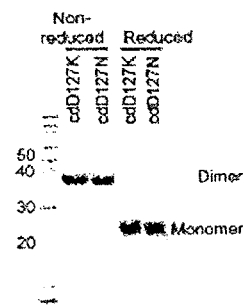

A free cysteine residue was introduced to the N-terminus of M2.2 D127N, which resulted in the formation of monomeric and dimeric species upon recombinant expression. The cystine-linked dimeric protein (termed cdDl27N) was purified from the monomer using size-exclusion chromatography. SDS-PAGE analysis of cdDl27N under reducing and non-reducing conditions confirmed that a dimer is formed through a covalent disulfide bond. (FIG. 16). Cystine-linked dimeric M2.2 D127K (termed cdD127K) and Aras-4 (termed cdAras-4) polypeptides were also generated.

4.3 Biological Activity of cdD127N, cdD127K, and cdAras-4 cdD127N and cdD127K exhibited agonistic activity at an order of magnitude lower concentration than the M2.2 D127N monomer which possesses similar agonistic activity to wild-type NK1 (FIG. 17). The agonist activity of cdD127K is surprising since the parental monomer, M2.2 D127K, is an antagonist. Similarly surprising is the result for cdAras-4 wherein the covalent linkage converted the antagonist Aras-4 into an agonist. The level of agonistic activity observed is approaches that of full-length HGF, however cdDl27N, cdDl27K, and cdAras-4 possess substantially improved stability relative to full length HGF and can be recombinantly expressed in yeast.

4.4 Only an N-Terminal Cysteine Mediates Homodimerization Directly

Based on the crystal structure of NK1 homodimers, it was recognized that position 127 is in close proximity on adjacent promoters. This suggested the possibility of forming covalently linked homodimers by placing a cysteine residue at this position. To test this possibility, a variant Aras-4 polypeptide was generated in which the residue D127 was substituted with Cys. The resulting polypeptides largely failed to produce dimers either spontaneously or after phenathroline-cupric sulfate treatment as shown in FIG. 18.

In addition to the covalent linkage through the addition of a free cysteine at the N-terminus of NK1 and variants, other locations and linkers where tested. (FIG. 19). A free cysteine or a combination of a free cysteine with a cysteine tag (Backer et al. (2006) *Nat. Med.* 13(4):504-509) were attached to the N-terminus or C-terminus of the Aras-4 variant. Only the free cysteine at the N-terminus resulted in dimeric protein upon recombinant expression in yeast.

5.0 Preparation of HGF Variant Polypeptides Containing Heparin Alginate Pellets Calcium alginate pellets may provide a stable platform for HGF because of enhanced retention of activity and storage time and thus can be used as devices for controlled HGF variant release. Heparin-sepharose beads (Pharmacia LKB) can be sterilized under ultraviolet light for 30 minutes and then mixed with filter-sterilized sodium alginate. The mixed slurry can then be dropped through a needle into a beaker containing a hardened solution of $CaCl_2$ (1.5% wt/vol.). Beads can form instantly. Cross-linked capsule envelopes can be obtained by incubating the capsules in the $CaCl_2$ solution for 5 minutes under gentle mixing and then for 10 minutes without mixing. The formed beads can be washed with sterile water and stored in 0.9% NaCl-1 mmol/L $CaCl_2$ at 4° C. HGF loading may be performed by incubating 10 capsules in 0.9% NaCl-1 mmol/L $CaCl_2$-0.05% gelatin with 12.5 µg (for 10 µg dose) or 125 µg (for 100 µg dose) or HGF variant for 16 hours under gentle agitation at 4° C. The end product may be sterilized under ultraviolet light for 30 minutes.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in their entirety.

What is claimed is:

1. A variant of human Hepatocyte Growth Factor (hHGF, SEQ ID NO: 1) having amino acid substitutions: K62E, N127D/A/K/R, K137R, K170E, and N193D.

2. The variant according to claim 1, wherein said variant is an antagonist of Met.

3. The variant according to claim 1, wherein said variant is an agonist of Met.

4. The variant according to claim 1, wherein said variant is conjugated to a member selected from the group consisting of a detectable moiety, a water-soluble polymer, a water-insoluble polymer, a therapeutic moiety, a targeting moiety and a combination thereof.

5. A pharmaceutical formulation comprising a variant according to claim 1, wherein said variant is in combination with a pharmaceutically acceptable carrier.

6. A variant of human Hepatocyte Growth Factor (hHGF, SEQ ID NO: 1) according to claim 1 further comprising amino acid substitutions at one or more of positions 64, 77, 95, 125, 130, 132, 142, 148, 154, and 173.

7. The variant according to claim 1, wherein said variant is conjugated to a diagnostic imaging agent.

8. A variant of human Hepatocyte Growth Factor (hHGF, SEQ ID NO: 1) comprising a sequence selected from the group consisting of SEQ ID NOs: 2-22, wherein said variant is conjugated to a diagnostic imaging agent.

9. A pharmaceutical formulation comprising a variant according to claim 8, wherein said variant is in combination with a pharmaceutically acceptable carrier.

10. A variant of human Hepatocyte Growth Factor (hHGF, SEQ ID NO: 1) having amino acid substitutions K62E, Q95R, I125T, N127D/A/K/R, I130V, K132N/R, K137R, K170E, Q173R, and N193D.

11. A variant of human Hepatocyte Growth Factor (hHGF, SEQ ID NO: 1) according to claim 10 further comprising amino acid substitutions at one or more of positions 64, 77, 142, 148, and 154.

12. A pharmaceutical formulation comprising a variant according to claim 10, wherein said variant is in combination with a pharmaceutically acceptable carrier.

13. A variant of human Hepatocyte Growth Factor (hHGF, SEQ ID NO: 1) having amino acid substitutions K62E, Q95R, K132N, K137R, K170E, Q173R, and N193D.

14. A variant of human Hepatocyte Growth Factor (hHGF, SEQ ID NO: 1) according to claim 13 further comprising amino acid substitutions at one or more of positions 64, 77, 125, 127, 130, 142, 148, and 154.

15. A pharmaceutical formulation comprising a variant according to claim 13, wherein said variant is in combination with a pharmaceutically acceptable carrier.

16. A variant of human Hepatocyte Growth Factor (hHGF, SEQ ID NO: 1) having amino acid substitutions K62E, Q95R, N127D/A/K/R, K132N/R, K137R, K170E, Q173R, and N193D.

17. A variant of human Hepatocyte Growth Factor (hHGF, SEQ ID NO: 1) according to claim 16 further comprising amino acid substitutions at one or more of positions 64, 77, 125, 130, 142, 148, and 154.

18. A pharmaceutical formulation comprising a variant according to claim 16, wherein said variant is in combination with a pharmaceutically acceptable carrier.

19. A variant of human Hepatocyte Growth Factor (hHGF, SEQ ID NO: 1) comprising a sequence selected form the group consisting of SEQ ID NOs: 2-22.

20. A pharmaceutical formulation comprising a variant according to claim 19, wherein said variant is in combination with a pharmaceutically acceptable carrier.

* * * * *

SEQUENCE LISTING

<160> NUMBER OF SEQ ID NOS: 24

<210> SEQ ID NO 1
<211> LENGTH: 728
<212> TYPE: PRT
<213> ORGANISM: Homo sapiens
<300> PUBLICATION INFORMATION:
<308> DATABASE ACCESSION NUMBER: GI/NP_000592
<309> DATABASE ENTRY DATE: 2003-08-19
<313> RELEVANT RESIDUES IN SEQ ID NO: (1)..(728)

<400> SEQUENCE: 1

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350
```

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
            435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 728
<212> TYPE: PRT
<213> ORGANISM: Homo sapiens

```
<400> SEQUENCE: 2

Met Trp Val Thr Lys Leu Leu Pro Ala Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Glu Ile Lys Thr Lys Lys Ala
50                  55                      60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asp Cys
                115                 120                 125

Ile Ile Gly Lys Gly Arg Ser Tyr Arg Gly Thr Val Ser Ile Thr Lys
130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
                180                 185                 190

Asp Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
                275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
                355                 360                 365

Asp Pro Asn Ile Arg Val Gly Tyr Cys Ser Gln Ile Pro Asn Cys Asp
                370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415
```

```
Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
            435                 440                 445

Gly Pro Trp Cys Tyr Thr Gly Asn Pro Leu Ile Pro Trp Asp Tyr Cys
            450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
                515                 520                 525

Val Leu Thr Ala Arg Gln Cys Phe Pro Ser Arg Asp Leu Lys Asp Tyr
            530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 3
<211> LENGTH: 728
<212> TYPE: PRT
<213> ORGANISM: Homo sapiens

<400> SEQUENCE: 3

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Glu Lys Ala
```

-continued

```
                50                  55                  60
Asn Thr Ala Asp Gln Cys Ala Asn Arg Cys Ile Arg Asn Lys Gly Leu
 65                  70                  75                  80

Pro Phe Thr Cys Lys Ala Phe Val Phe Asp Lys Ala Arg Lys Arg Cys
                     85                  90                  95

Leu Trp Phe Pro Val Asn Ser Met Ser Ser Gly Val Lys Lys Glu Phe
                100                 105                 110

Gly His Glu Phe Asp Leu Tyr Glu Asn Lys Asp Tyr Thr Arg Asn Cys
                115                 120                 125

Ile Val Gly Asn Gly Arg Ser Tyr Arg Gly Thr Val Ser Thr Thr Lys
            130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
                180                 185                 190

Asp Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
                275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
                355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
                435                 440                 445

Gly Pro Trp Cys Tyr Thr Gly Asn Pro Leu Ile Pro Trp Asp Tyr Cys
                450                 455                 460

Pro Ile Ser Arg Cys Glu Gly Asp Thr Thr Pro Thr Ile Val Asn Leu
465                 470                 475                 480
```

```
Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 4
<211> LENGTH: 728
<212> TYPE: PRT
<213> ORGANISM: Homo sapiens

<400> SEQUENCE: 4

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
```

```
              115                 120                 125
Ile Val Gly Asn Gly Arg Ser Tyr Arg Gly Thr Val Ser Ile Thr Lys
              130                 135                 140
Ser Gly Ile Glu Cys Gln Pro Trp Ser Ala Met Ile Pro His Glu His
145                 150                 155                 160
Ser Phe Leu Pro Ser Ser Tyr Arg Gly Glu Asp Leu Arg Glu Asn Tyr
              165                 170                 175
Cys Arg Asn Pro Arg Gly Glu Glu Gly Gly Pro Trp Cys Tyr Thr Ser
              180                 185                 190
Asp Pro Glu Val Arg Tyr Glu Val Cys Asp Ile Pro Gln Cys Ser Glu
              195                 200                 205
Val Glu Cys Met Thr Cys Asn Gly Glu Ser Tyr Arg Gly Leu Met Asp
              210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
              245                 250                 255
Asp Asn Tyr Cys Arg Asn Pro Asp Gly Gln Pro Arg Pro Trp Cys Tyr
              260                 265                 270
Thr Leu Asp Pro His Thr Arg Trp Glu Tyr Cys Ala Ile Lys Thr Cys
              275                 280                 285
Ala Asp Asn Thr Met Asn Asp Thr Asp Val Pro Leu Glu Thr Thr Glu
              290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
              325                 330                 335
His Asp Met Thr Pro Glu Asn Phe Lys Cys Lys Asp Leu Arg Glu Asn
              340                 345                 350
Tyr Cys Arg Asn Pro Asp Gly Ser Glu Ser Pro Trp Cys Phe Thr Thr
              355                 360                 365
Asp Pro Asn Ile Arg Val Gly Tyr Cys Ser Gln Ile Pro Asn Cys Asp
              370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
              405                 410                 415
Lys Asn Met Glu Asp Leu His Arg His Ile Phe Trp Glu Pro Asp Ala
              420                 425                 430
Ser Lys Leu Asn Glu Asn Tyr Cys Arg Asn Pro Asp Asp Ala His
              435                 440                 445
Gly Pro Trp Cys Tyr Thr Gly Asn Pro Leu Ile Pro Trp Asp Tyr Cys
              450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
              485                 490                 495
Asn Gly Ile Pro Thr Arg Thr Asn Ile Gly Trp Met Val Ser Leu Arg
              500                 505                 510
Tyr Arg Asn Lys His Ile Cys Gly Gly Ser Leu Ile Lys Glu Ser Trp
              515                 520                 525
Val Leu Thr Ala Arg Gln Cys Phe Pro Ser Arg Asp Leu Lys Asp Tyr
              530                 535                 540
```

```
Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 5
<211> LENGTH: 728
<212> TYPE: PRT
<213> ORGANISM: Homo sapiens

<400> SEQUENCE: 5

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Lys Gly Gln
            20                  25                  30

Gly Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asp Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Val Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
```

```
                180                 185                 190
Asp Pro Glu Val Arg Tyr Glu Val Cys Asp Ile Pro Gln Cys Ser Glu
            195                 200                 205
Val Glu Cys Met Thr Cys Asn Gly Glu Ser Tyr Arg Gly Leu Met Asp
            210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
            260                 265                 270
Thr Leu Asp Pro His Thr Arg Trp Glu Tyr Cys Ala Ile Lys Thr Cys
            275                 280                 285
Ala Asp Asn Thr Met Asn Asp Thr Asp Val Pro Leu Glu Thr Thr Glu
            290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
            340                 345                 350
Tyr Cys Arg Asn Pro Asp Gly Ser Glu Ser Pro Trp Cys Phe Thr Thr
            355                 360                 365
Asp Pro Asn Ile Arg Val Gly Tyr Cys Ser Gln Ile Pro Asn Cys Asp
            370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
            435                 440                 445
Gly Pro Trp Cys Tyr Thr Gly Asn Pro Leu Ile Pro Trp Asp Tyr Cys
            450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
            515                 520                 525
Val Leu Thr Ala Arg Gln Cys Phe Pro Ser Arg Asp Leu Lys Asp Tyr
            530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
            595                 600                 605
```

```
Lys Thr Ser Cys Ser Val Tyr Gly Trp Gly Tyr Thr Gly Leu Ile Asn
            610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 6
<211> LENGTH: 728
<212> TYPE: PRT
<213> ORGANISM: Homo sapiens

<400> SEQUENCE: 6

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Ala Ile His Glu Phe Lys Lys Ser Ala Lys Ala
        35                  40                  45

Thr Leu Ile Lys Ile Asp Pro Ala Leu Lys Ile Lys Thr Glu Lys Ala
50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Ile Thr Lys
    130                 135                 140

Ser Gly Ile Glu Cys Gln Pro Trp Ser Ser Met Ile Pro His Glu His
145                 150                 155                 160

Ser Phe Leu Pro Ser Ser Tyr Arg Gly Glu Asp Leu Gln Glu Asn Tyr
                165                 170                 175

Cys Arg Asn Pro Trp Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
```

```
                    245                 250                 255
Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670
```

```
Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 7
<211> LENGTH: 728
<212> TYPE: PRT
<213> ORGANISM: Homo sapiens

<400> SEQUENCE: 7

Met Trp Val Thr Lys Leu Leu Pro Ala Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Glu Lys Ala
50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Thr Arg Asn Cys
            115                 120                 125

Ile Val Gly Asn Gly Arg Ser Tyr Arg Gly Thr Val Ser Ile Thr Lys
            130                 135                 140

Ser Gly Ile Glu Cys Gln Pro Trp Ser Ala Met Ile Pro His Glu His
145                 150                 155                 160

Ser Phe Leu Pro Ser Ser Tyr Gln Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
            210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
```

```
        305                 310                 315                 320
Trp Asn Gly Ile Pro Cys Gln Arg Trp Asp Ser Gln Tyr Pro His Glu
                    325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
        370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
        530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
        610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

<210> SEQ ID NO 8
<211> LENGTH: 728
<212> TYPE: PRT
<213> ORGANISM: Homo sapiens

<400> SEQUENCE: 8

Met Trp Val Thr Lys Leu Leu Pro Ala Leu Leu Gln His Val Leu
1               5                   10                  15

Leu His Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp

```
                370                 375                 380
Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
        530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
        610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 9
<211> LENGTH: 728
<212> TYPE: PRT
<213> ORGANISM: Homo sapiens

<400> SEQUENCE: 9

Met Trp Val Thr Lys Leu Leu Pro Ala Leu Leu Leu Gln His Val Leu
1               5                   10                  15
```

```
Leu His Leu Leu Leu Leu Pro Ile Ala Ile Pro Tyr Ala Glu Gly Gln
             20                  25                  30

Arg Lys Arg Arg Asp Ala Ile His Glu Cys Lys Arg Ser Ala Lys Thr
         35                  40                  45

Thr Leu Ile Lys Ile Asp Pro Ala Leu Lys Ile Lys Thr Glu Lys Ala
     50                  55                  60

Asn Thr Ala Asp Gln Cys Ala Asn Arg Cys Thr Arg Asn Lys Gly Leu
 65                  70                  75                  80

Pro Ser Thr Cys Lys Ala Phe Val Phe Asp Lys Ala Arg Lys Arg Arg
                 85                  90                  95

Leu Arg Phe Pro Phe Asn Ser Met Ser Ser Gly Val Lys Lys Glu Phe
             100                 105                 110

Gly His Glu Phe Asp Leu Tyr Glu Asn Lys Asp Tyr Thr Arg Asn Cys
         115                 120                 125

Ile Val Gly Lys Gly Arg Ser Tyr Arg Gly Thr Val Ser Thr Thr Lys
     130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
             165                 170                 175

Cys Arg Asn Pro Arg Gly Glu Glu Gly Gly Pro Trp Cys Tyr Thr Ser
             180                 185                 190

Asp Pro Glu Val Arg Tyr Glu Val Cys Asp Ile Pro Gln Cys Ser Glu
         195                 200                 205

Val Glu Cys Met Thr Cys Asn Gly Glu Ser Tyr Arg Gly Leu Met Asp
     210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
             245                 250                 255

Asp Asn Tyr Cys Arg Asn Pro Asp Gly Gln Pro Arg Pro Trp Cys Tyr
             260                 265                 270

Thr Leu Asp Pro His Thr Arg Trp Glu Tyr Cys Ala Ile Lys Thr Cys
     275                 280                 285

Ala Asp Asn Thr Met Asn Asp Thr Asp Val Pro Leu Glu Thr Thr Glu
 290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
             325                 330                 335

His Asp Met Thr Pro Glu Asn Phe Lys Cys Lys Asp Leu Arg Glu Asn
         340                 345                 350

Tyr Cys Arg Asn Pro Asp Gly Ser Glu Ser Pro Trp Cys Phe Thr Thr
     355                 360                 365

Asp Pro Asn Ile Arg Val Gly Tyr Cys Ser Gln Ile Pro Asn Cys Asp
 370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
             405                 410                 415

Lys Asn Met Glu Asp Leu His Arg His Ile Phe Trp Glu Pro Asp Ala
         420                 425                 430

Ser Lys Leu Asn Glu Asn Tyr Cys Arg Asn Pro Asp Asp Asp Ala His
```

```
                435                 440                 445
Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 10
<211> LENGTH: 728
<212> TYPE: PRT
<213> ORGANISM: Homo sapiens

<400> SEQUENCE: 10

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Gly Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Glu Lys Val
        50                  55                  60

Asn Thr Ala Asp Gln Cys Ala Asn Arg Cys Thr Arg Ser Lys Gly Leu
65                  70                  75                  80
```

-continued

```
Pro Phe Thr Cys Lys Ala Phe Val Phe Asp Lys Ala Arg Lys Arg Cys
             85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
            115                 120                 125

Ile Ile Gly Arg Gly Arg Ser Tyr Arg Gly Thr Val Ser Ile Thr Lys
            130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
            370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
            450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
```

```
                    500                 505                 510
Tyr Arg Asn Lys His Ile Cys Gly Gly Ser Leu Ile Lys Glu Ser Trp
                515                 520                 525

Val Leu Thr Ala Arg Gln Cys Phe Pro Ser Arg Asp Leu Lys Asp Tyr
            530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
            610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 11
<211> LENGTH: 728
<212> TYPE: PRT
<213> ORGANISM: Homo sapiens

<400> SEQUENCE: 11

Met Trp Val Thr Lys Leu Leu Pro Ala Leu Leu Leu Gln His Val Leu
1               5                   10                  15

Leu His Leu Leu Leu Leu Pro Ile Ala Ile Pro His Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Thr Arg Asn Cys
        115                 120                 125

Ile Val Gly Asn Gly Arg Ser Tyr Arg Gly Thr Val Ser Thr Thr Lys
    130                 135                 140
```

-continued

```
Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
            165                 170                 175

Cys Arg Asn Pro Arg Gly Glu Glu Gly Gly Pro Trp Cys Tyr Thr Ser
                180                 185                 190

Asp Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
            370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
```

```
                         565                 570                 575
Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
            610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
            645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
            725

<210> SEQ ID NO 12
<211> LENGTH: 728
<212> TYPE: PRT
<213> ORGANISM: Homo sapiens

<400> SEQUENCE: 12

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Arg Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Asn Gly Arg Ser Tyr Arg Gly Thr Val Ser Val Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205
```

```
Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
```

```
                   625                 630                 635                 640
Lys Cys Ser Gln His His Arg Gly Lys Val Thr Leu Asn Glu Ser Glu
                        645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 13
<211> LENGTH: 728
<212> TYPE: PRT
<213> ORGANISM: Homo sapiens

<400> SEQUENCE: 13

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270
```

```
Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
```

-continued

```
                690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 14
<211> LENGTH: 728
<212> TYPE: PRT
<213> ORGANISM: Homo sapiens

<400> SEQUENCE: 14

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
                20                  25                  30

Arg Lys Arg Arg Asn Thr Ile His Glu Phe Lys Lys Ser Val Lys Thr
                35                  40                  45

Thr Leu Ile Lys Ile Asp Pro Ala Leu Lys Ile Lys Thr Glu Lys Ala
        50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Val Asn Ser Met Ser Ser Gly Val Lys Lys Glu Ser
                100                 105                 110

Gly His Glu Phe Asp Leu Tyr Glu Asn Lys Asp Tyr Ile Arg Asp Cys
                115                 120                 125

Ile Val Gly Asn Gly Arg Ser Tyr Arg Gly Thr Val Ser Thr Thr Lys
            130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
                180                 185                 190

Asp Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
                275                 280                 285

Ala Asp Asn Thr Met Asn Asp Thr Asp Val Pro Leu Glu Thr Thr Glu
            290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335
```

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 15
<211> LENGTH: 728
<212> TYPE: PRT

<213> ORGANISM: Homo sapiens

<400> SEQUENCE: 15

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Trp Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400
```

```
Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 16
<211> LENGTH: 728
<212> TYPE: PRT
<213> ORGANISM: Homo sapiens

<400> SEQUENCE: 16

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45
```

```
Thr Leu Ile Lys Ile Asp Pro Ala Leu Arg Ile Lys Thr Glu Lys Ala
    50                  55                  60

Asn Thr Ala Asp Gln Cys Ala Asn Arg Cys Thr Arg Ser Arg Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asp Cys
                115                 120                 125

Ile Ile Gly Asn Gly Arg Ser Tyr Arg Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
                180                 185                 190

Asp Pro Glu Val Arg Tyr Glu Val Cys Asp Ile Pro Gln Cys Ser Glu
                195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
                275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
                355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
                435                 440                 445

Gly Pro Trp Cys Tyr Thr Gly Asn Pro Leu Ile Pro Trp Asp Tyr Cys
    450                 455                 460
```

```
Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
        530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 17
<211> LENGTH: 728
<212> TYPE: PRT
<213> ORGANISM: Homo sapiens

<400> SEQUENCE: 17

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Arg Arg Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110
```

```
Gly His Glu Phe Asp Leu Tyr Glu Asn Lys Asp Tyr Ile Arg Asp Cys
    115                 120                 125

Ile Ile Gly Lys Gly Arg Ser Tyr Arg Gly Thr Val Ser Val Thr Lys
    130                 135                 140

Ser Gly Ile Glu Cys Gln Pro Trp Ser Ala Met Ile Pro His Glu His
145                 150                 155                 160

Ser Phe Leu Pro Ser Asn Tyr Arg Gly Glu Asp Leu Arg Glu Asn Tyr
                165                 170                 175

Cys Arg Asn Pro Arg Gly Glu Glu Gly Pro Trp Cys Tyr Thr Ser
                180                 185                 190

Asp Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
        370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525
```

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 18
<211> LENGTH: 728
<212> TYPE: PRT
<213> ORGANISM: Homo sapiens

<400> SEQUENCE: 18

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Ile Thr Lys
    130                 135                 140

Ser Gly Ile Glu Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

```
Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
                275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
                355                 360                 365

Asp Pro Asn Ile Arg Val Gly Tyr Cys Ser Gln Ile Pro Asn Cys Asp
                370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
                435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
                515                 520                 525

Val Leu Thr Ala Arg Gln Cys Phe Pro Ser Arg Asp Leu Lys Asp Tyr
                530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590
```

```
Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 19
<211> LENGTH: 728
<212> TYPE: PRT
<213> ORGANISM: Homo sapiens

<400> SEQUENCE: 19

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
    50                  55                  60

Asp Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Asn Gly Arg Ser Tyr Arg Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240
```

-continued

```
His Arg His Lys Phe Leu Pro Glu Arg Tyr Pro Asp Lys Gly Phe Asp
            245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
        370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
        530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
        610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655
```

```
Ile Cys Ala Gly Ala Glu Lys Ile Gly Ser Pro Cys Glu Gly Asp
            660                 665                 670
Tyr Gly Gly Pro Leu Val Cys Glu Gln His Lys Met Arg Met Val Leu
            675                 680                 685
Gly Val Ile Val Pro Gly Arg Gly Cys Ala Ile Pro Asn Arg Pro Gly
            690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725

<210> SEQ ID NO 20
<211> LENGTH: 728
<212> TYPE: PRT
<213> ORGANISM: Homo sapiens

<400> SEQUENCE: 20

Met Trp Val Thr Lys Leu Leu Pro Ala Leu Leu Leu Gln His Val Leu
1                   5                   10                  15
Leu His Leu Leu Leu Leu Pro Ile Ala Ile Pro Tyr Ala Glu Gly Gln
                20                  25                  30
Gly Lys Arg Arg Asn Thr Ile His Glu Phe Lys Lys Ser Ala Lys Thr
            35                  40                  45
Thr Leu Ile Lys Ile Asp Pro Ala Leu Arg Ile Lys Thr Glu Lys Ala
        50                  55                  60
Asn Thr Ala Asp Gln Cys Ala Asn Arg Cys Thr Arg Ser Lys Gly Leu
65                  70                  75                  80
Pro Phe Thr Cys Lys Ala Phe Val Phe Asp Lys Ala Arg Lys Arg Cys
                85                  90                  95
Leu Trp Phe Pro Phe Asn Ser Met Ser Ser Gly Val Lys Lys Glu Phe
            100                 105                 110
Gly His Glu Phe Asp Leu Tyr Glu Asn Lys Ala Tyr Ile Arg Asp Cys
        115                 120                 125
Ile Ile Gly Arg Gly Arg Asn Tyr Arg Gly Thr Val Ser Ile Thr Lys
130                 135                 140
Ser Gly Ile Lys Cys Gln Pro Trp Ser Ala Met Ile Pro His Glu His
145                 150                 155                 160
Ser Phe Leu Pro Ser Ser Tyr Arg Gly Glu Asp Leu Arg Glu Asn Tyr
                165                 170                 175
Cys Arg Asn Pro Arg Gly Glu Glu Gly Gly Pro Trp Cys Tyr Thr Ser
            180                 185                 190
Asp Pro Glu Val Arg Tyr Glu Val Cys Asp Ile Pro Gln Cys Ser Glu
        195                 200                 205
Val Glu Cys Met Thr Cys Asn Gly Glu Ser Tyr Arg Gly Leu Met Asp
210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
            260                 265                 270
Thr Leu Asp Pro His Thr Arg Trp Glu Tyr Cys Ala Ile Lys Thr Cys
        275                 280                 285
Ala Asp Asn Thr Met Asn Asp Thr Asp Val Pro Leu Glu Thr Thr Glu
        290                 295                 300
```

```
Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
            325                 330                 335

His Asp Met Thr Pro Glu Asn Phe Lys Cys Lys Asp Leu Arg Glu Asn
        340                 345                 350

Tyr Cys Arg Asn Pro Asp Gly Ser Glu Ser Pro Trp Cys Phe Thr Thr
    355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
            405                 410                 415

Lys Asn Met Glu Asp Leu His Arg His Ile Phe Trp Glu Pro Asp Ala
        420                 425                 430

Ser Lys Leu Asn Glu Asn Tyr Cys Arg Asn Pro Asp Asp Asp Ala His
    435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
        500                 505                 510

Tyr Arg Asn Lys His Ile Cys Gly Gly Ser Leu Ile Lys Glu Ser Trp
    515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
            565                 570                 575

Ser Asp Leu Val Leu Met Lys Leu Ala Arg Pro Ala Val Leu Asp Asp
        580                 585                 590

Phe Val Ser Thr Ile Asp Leu Pro Asn Tyr Gly Cys Thr Ile Pro Glu
    595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
            645                 650                 655

Ile Cys Ala Gly Ala Glu Lys Ile Gly Ser Gly Pro Cys Glu Gly Asp
        660                 665                 670

Tyr Gly Gly Pro Leu Val Cys Glu Gln His Lys Met Arg Met Val Leu
    675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720
```

```
Leu Thr Tyr Lys Val Pro Gln Ser
            725

<210> SEQ ID NO 21
<211> LENGTH: 728
<212> TYPE: PRT
<213> ORGANISM: Homo sapiens

<400> SEQUENCE: 21

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Lys Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Glu Ile Lys Thr Glu Lys Val
        50                  55                  60

Asn Thr Ala Asp Gln Cys Ala Asn Arg Cys Ile Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Ala Tyr Ile Arg Asp Cys
        115                 120                 125

Ile Ile Gly Arg Gly Arg Asn Tyr Arg Gly Thr Val Ser Ile Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365
```

Asp Pro Asn Ile Arg Val Gly Tyr Cys Ser Gln Ile Pro Asn Cys Asp
                370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 22
<211> LENGTH: 728
<212> TYPE: PRT
<213> ORGANISM: Homo sapiens

<400> SEQUENCE: 22

Met Trp Val Thr Lys Leu Leu Pro Ala Leu Leu Leu Gln His Val Leu

```
1               5                   10                  15
Leu His Leu Leu Leu Pro Ile Ala Ile Pro Tyr Ala Glu Gly Gln
             20                  25                  30

Gly Lys Arg Arg Asn Thr Ile His Glu Phe Lys Lys Ser Ala Lys Thr
             35                  40                  45

Thr Leu Ile Lys Ile Asp Pro Ala Leu Lys Ile Lys Thr Glu Lys Val
             50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                    85                  90                  95

Leu Trp Phe Pro Phe Asn Ser Met Ser Ser Gly Val Lys Lys Glu Phe
                    100                 105                 110

Gly His Glu Phe Asp Leu Tyr Glu Asn Lys Asp Tyr Ile Arg Asp Cys
                    115                 120                 125

Ile Ile Gly Asn Gly Arg Ser Tyr Arg Gly Thr Val Ser Ile Thr Lys
             130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                    165                 170                 175

Cys Arg Asn Pro Arg Gly Glu Glu Gly Pro Trp Cys Tyr Thr Ser
                    180                 185                 190

Asp Pro Glu Val Arg Tyr Glu Val Cys Asp Ile Pro Gln Cys Ser Glu
             195                 200                 205

Val Glu Cys Met Thr Cys Asn Gly Glu Ser Tyr Arg Gly Leu Met Asp
             210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                    245                 250                 255

Asp Asn Tyr Cys Arg Asn Pro Asp Gly Gln Pro Arg Pro Trp Cys Tyr
                    260                 265                 270

Thr Leu Asp Pro His Thr Arg Trp Glu Tyr Cys Ala Ile Lys Thr Cys
             275                 280                 285

Ala Asp Asn Thr Met Asn Asp Thr Asp Val Pro Leu Glu Thr Thr Glu
             290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                    325                 330                 335

His Asp Met Thr Pro Glu Asn Phe Lys Cys Lys Asp Leu Arg Glu Asn
                    340                 345                 350

Tyr Cys Arg Asn Pro Asp Gly Ser Glu Ser Pro Trp Cys Phe Thr Thr
                    355                 360                 365

Asp Pro Asn Ile Arg Val Gly Tyr Cys Ser Gln Ile Pro Asn Cys Asp
             370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                    405                 410                 415

Lys Asn Met Glu Asp Leu His Arg His Ile Phe Trp Glu Pro Asp Ala
             420                 425                 430
```

```
Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 23
<211> LENGTH: 723
<212> TYPE: PRT
<213> ORGANISM: Homo sapiens
<300> PUBLICATION INFORMATION:
<308> DATABASE ACCESSION NUMBER: GI/NP_001010932
<309> DATABASE ENTRY DATE: 2008-07-01
<313> RELEVANT RESIDUES IN SEQ ID NO: (1)..(723)

<400> SEQUENCE: 23

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45
```

```
Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
 65              70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Asp Ala His Gly Pro Trp Cys Tyr
        435                 440                 445

Thr Gly Asn Pro Leu Ile Pro Trp Asp Tyr Cys Pro Ile Ser Arg Cys
450                 455                 460

Glu Gly Asp Thr Thr Pro Thr Ile Val Asn Leu Asp His Pro Val Ile
```

```
              465                 470                 475                 480
Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
                500                 505                 510

Ile Cys Gly Gly Ser Leu Ile Lys Glu Ser Trp Val Leu Thr Ala Arg
                515                 520                 525

Gln Cys Phe Pro Ser Arg Asp Leu Lys Asp Tyr Glu Ala Trp Leu Gly
                530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
                580                 585                 590

Asp Leu Pro Asn Tyr Gly Cys Thr Ile Pro Glu Lys Thr Ser Cys Ser
                595                 600                 605

Val Tyr Gly Trp Gly Tyr Thr Gly Leu Ile Asn Tyr Asp Gly Leu Leu
610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
                660                 665                 670

Val Cys Glu Gln His Lys Met Arg Met Val Leu Gly Val Ile Val Pro
                675                 680                 685

Gly Arg Gly Cys Ala Ile Pro Asn Arg Pro Gly Ile Phe Val Arg Val
                690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 24
<211> LENGTH: 14
<212> TYPE: PRT
<213> ORGANISM: Artificial Sequence
<220> FEATURE:
<223> OTHER INFORMATION: Linker amino acid

<400> SEQUENCE: 24

Lys Glu Ser Cys Ala Lys Lys Gln Arg Gln His Met Asp Ser
1               5                   10
```